United States Patent
Neben et al.

(10) Patent No.: US 12,376,828 B2
(45) Date of Patent: Aug. 5, 2025

(54) METHODS AND SYSTEMS FOR COHERENCE IMAGING IN OBTAINING ULTRASOUND IMAGES

(71) Applicant: BFLY OPERATIONS, INC., Burlington, MA (US)

(72) Inventors: Abraham Neben, Guilford, CT (US); Samuel Cherna, West Orange, NJ (US); Karl Thiele, St. Petersburg, FL (US)

(73) Assignee: BFLY OPERATIONS, INC., Burlington, MA (US)

( * ) Notice: Subject to any disclaimer, the term of this patent is extended or adjusted under 35 U.S.C. 154(b) by 707 days.

(21) Appl. No.: 17/525,791

(22) Filed: Nov. 12, 2021

(65) Prior Publication Data

US 2022/0330917 A1    Oct. 20, 2022

Related U.S. Application Data

(60) Provisional application No. 63/176,724, filed on Apr. 19, 2021.

(51) Int. Cl.
*A61B 8/00* (2006.01)
*A61B 5/00* (2006.01)

(52) U.S. Cl.
CPC .......... *A61B 8/4472* (2013.01); *A61B 5/0066* (2013.01); *A61B 8/4427* (2013.01)

(58) Field of Classification Search
CPC .................................................. A61B 8/4472
See application file for complete search history.

(56) References Cited

U.S. PATENT DOCUMENTS

| 8,852,103 B2 | 10/2014 | Rothberg et al. |
| 9,521,991 B2 | 12/2016 | Rothberg et al. |

(Continued)

FOREIGN PATENT DOCUMENTS

| EM | 008368500-0001 S | 12/2020 | |
| WO | WO-2018175905 A1 * | 9/2018 | ........... A61B 8/4427 |

OTHER PUBLICATIONS

International Search Report and Written Opinion mailed Jun. 29, 2022 in connection with International Application No. PCT/US22/25207.

(Continued)

*Primary Examiner* — Joseph M Santos Rodriguez
(74) *Attorney, Agent, or Firm* — Carter, DeLuca & Farrell LLP; Vadim Vapnyar

(57) ABSTRACT

A system for coherence imaging may receive ultrasound signals each having a respective delay associated with a respective ultrasonic transducer element in an ultrasonic transducer array. The system may obtain an approximation of the auto-correlation of ultrasound signals without any auto-correlation calculation, and determine the output image based on the approximation. In approximating the auto-correlation, the system may group the ultrasound signals into multiple portions, each corresponding to a respective sub-aperture of a plurality of sub-apertures of the ultrasonic transducer array. The system may determine a coherent sum of signals for each sub-aperture, perform a square operation or magnitude square operation over the coherent sum to obtain resulting data, normalize the resulting data, and sum the resulting data for all of the sub-apertures to generate the output image. A sub-aperture in the plurality of sub-apertures may overlap with another sub-aperture.

13 Claims, 14 Drawing Sheets

(56) References Cited

U.S. PATENT DOCUMENTS

| | | |
|---|---|---|
| 9,592,030 B2 | 3/2017 | Rothberg et al. |
| 10,624,613 B2 | 4/2020 | Ralston |
| 10,856,840 B2 | 12/2020 | Rothberg et al. |
| 2005/0228279 A1 | 10/2005 | Ustuner et al. |
| 2011/0055447 A1 | 3/2011 | Costa |
| 2013/0253325 A1* | 9/2013 | Call ............... G01S 15/8952 600/447 |
| 2014/0128740 A1 | 5/2014 | Chiang et al. |
| 2015/0366542 A1 | 12/2015 | Brown et al. |
| 2017/0307741 A1 | 10/2017 | Ralston et al. |
| 2017/0360402 A1 | 12/2017 | de Jonge et al. |
| 2019/0142388 A1 | 5/2019 | Gonyeau et al. |
| 2019/0307428 A1 | 10/2019 | Silverman et al. |
| 2019/0388059 A1 | 12/2019 | Pelissier et al. |
| 2020/0129151 A1 | 4/2020 | Neben et al. |
| 2020/0155113 A1 | 5/2020 | Neben et al. |
| 2020/0253585 A1 | 8/2020 | Neben et al. |
| 2020/0320694 A1 | 10/2020 | Howell et al. |
| 2020/0390419 A1 | 12/2020 | Neben et al. |
| 2020/0405271 A1 | 12/2020 | Chiu et al. |
| 2021/0000450 A1 | 1/2021 | Zhang et al. |
| 2021/0015456 A1 | 1/2021 | Chiang et al. |
| 2021/0038199 A1 | 2/2021 | Neben et al. |
| 2021/0153846 A1 | 5/2021 | Bellamkonda et al. |
| 2021/0196237 A1 | 7/2021 | Bellamkonda et al. |
| 2021/0330295 A1 | 10/2021 | Soleimani et al. |

OTHER PUBLICATIONS

Hyun et al., Efficient strategies for estimating the spatial coherence of backscatter. IEEE transactions on ultrasonics, ferroelectrics, and frequency control. Dec. 1, 2016;64(3):500-13.

Extended European Search Report issued in corresponding application EP 22792264.8 dated Jan. 29, 2025 (13 pages).

Masume Sadeghi, et al. "Improving beamforming performance by phased synthetic aperture imaging in medical ultrasound", Journal of Medical Ultrasonics, vol. 44, No. 1, Oct. 28, 2016, pp. 51-62.

\* cited by examiner

METHODS AND SYSTEMS FOR COHERENCE IMAGING IN OBTAINING ULTRASOUND IMAGES

CROSS-REFERENCE TO RELATED APPLICATIONS

This application claims the benefit under 35 U.S.C. § 119(e) of U.S. Provisional Application No. 63/176,724, filed Apr. 19, 2021, and entitled, "METHODS AND SYSTEMS FOR COHERENCE IMAGING IN OBTAINING ULTRASOUND IMAGES," which is hereby incorporated by reference herein in its entirety.

FIELD

Generally, the aspects of the technology described herein relate to ultrasound devices and methods. Some aspects relate to methods and systems for coherent ultrasound imaging in obtaining ultrasound images.

BACKGROUND

Ultrasound probes may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. In ultrasound imaging, an ultrasound probe may include an ultrasonic transducer array having multiple ultrasonic transducer elements. Each of the ultrasonic transducer elements may be capable of transmitting and receiving reflected ultrasound signals. These reflected ultrasound signals may then be received, processed and displayed as an image to the operator. The strength (amplitude) of the sound signal and the time it takes for the wave to travel through the body may provide information used to produce the ultrasound images.

SUMMARY

According to an aspect of the application, an apparatus is provided, comprising: a handheld ultrasound probe weighing less than 500 grams, having a length of less than 300 mm, and being wirelessly operatively couplable to a smartphone or tablet. The handheld ultrasound probe contains: an ultrasonic transducer array configured to selectively transmit ultrasound signals at any frequency from 1 MHz-12 MHz associated with a plurality of transducer elements and receive ultrasound signals reflected through a target tissue and one or more processing devices. The one or more processing devices are configured to, for a point in the target tissue: process a plurality of portions of received signals associated with the point in the target tissue, wherein each of the plurality of portions is associated with a respective one of a plurality of sub-apertures of the transducer array. The processing comprises: determining a respective coherent sum over each of the plurality of portions of the received signals; performing a processing operation over the respective coherent sum to obtain respective resulting data for each sub-aperture; and summing the resulting data for the plurality of sub-apertures for imaging the target tissue.

According to an aspect of the present application, a method of processing ultrasound signals received by an ultrasonic transducer array for imaging a target tissue is provided. The method comprises, for a point in the target tissue: processing a plurality of portions of ultrasound signals associated with the point in the target tissue, wherein each of the plurality of portions corresponds to a respective one of a plurality of sub-apertures of the transducer array, and wherein the received ultrasound signals are each delayed by a respective delay time. The processing comprises: determining a respective coherent sum over each of the plurality of portions of the ultrasound signals; and performing a processing operation over the respective coherent sum to obtain respective resulting data for each sub-aperture. The method further comprises determining output data for imaging the target tissue at the point by summing the resulting data for the plurality of sub-apertures.

According to an aspect of the present application, a method of processing ultrasound signals received by an ultrasonic transducer array comprising a plurality of transducer elements is provided. The method comprises receiving ultrasound signals with the plurality of transducer elements of the ultrasonic transducer array, wherein the received ultrasound signals are reflected from a target tissue; delaying the received ultrasound signals each by a respective delay time; approximating a correlation of the received ultrasound signals from the plurality of transducer elements without performing any correlation calculation; and determining an image of a target issue based in part on the approximated correlation.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1A:
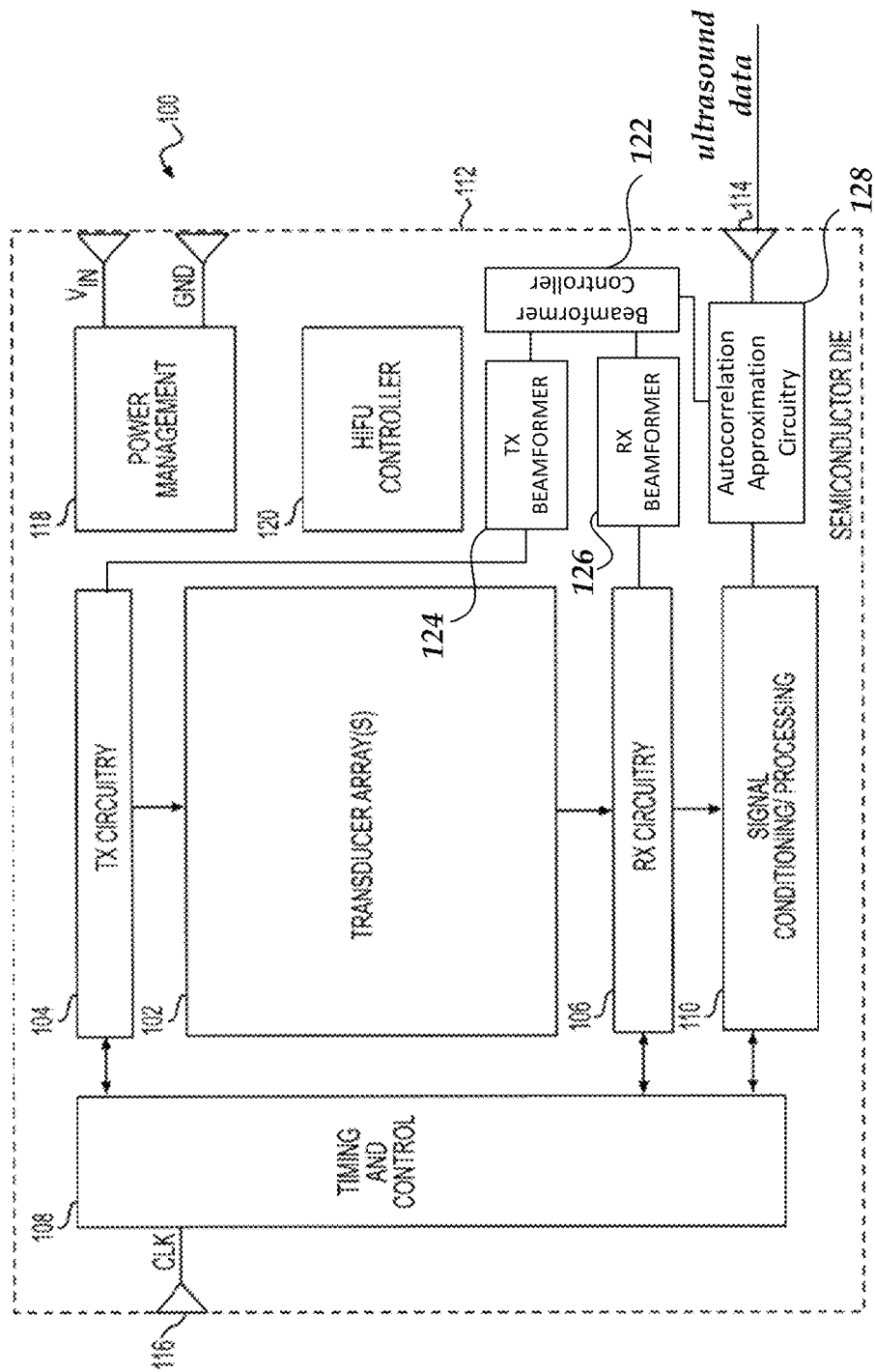
FIG. 1A is a block diagram of an example of an ultrasound device including a beamformer that may be used to perform an approximation function of a coherence imaging process, in accordance with some embodiments of the technology described herein.

Some ultrasound imaging devices utilize delay-and-sum (DAS) techniques. In a receive beamforming operation, the signals received by the ultrasonic transducers of an ultrasound imaging device are delayed by a desirable per-transducer delay time, then summed to produce an image value. In this way, the receive field of view of the ultrasound imaging device is focused on echoes reflected from a focal point of interest. Transmit beamforming is also sometimes utilized, in which signals transmitted from the ultrasonic transducers of the ultrasound imaging device are delayed by respective amounts which result in a transmit beam focused at a focal point.

In some instances, coherence imaging is performed. Conventional DAS techniques are susceptible to detecting unwanted reflections which may produce clutter in the ultrasound image. Also, lower transmit pressure may result in lesser image quality. The drawbacks of DAS imaging may be heightened when performing cardiac ultrasound imaging. In some forms of coherence imaging, instead of taking the sum of received ultrasound signals as is done in the DAS technique, the spatial auto-correlation of received ultrasound signals is taken over various desirable distances (lags) among different ultrasonic transducers along the aperture. For example, the correlation of signals from transducers within short distances with respect to each other may be retained, while the correlation of signals from transducers that are farther apart may be ignored or removed. Performing such an auto-correlation can reduce the occurrence of clutter in the resulting ultrasound image.

Coherence imaging may be particularly useful in cardiac ultrasound imaging applications, particularly if the ultrasound probe being used has a sufficiently large transducer array prohibit fitting the probe neatly between the patient's ribs. Some patients naturally have little space between the ribs, such that the ultrasound probe being used may overlap one or more ribs. In some patients, the heart may be positioned in the thorax directly behind a rib. In either scenario, the ultrasound signals emitted by the ultrasound probe may interact with the patient's rib(s), leading to rib-induced artifacts in the resulting ultrasound image. Some systems attempt to reduce such artifacts by reducing the gain of the ultrasound signals, e.g., using time gain compensation (TGC). However, TGC techniques tend to suppress important information too. Therefore, coherence imaging is sometimes used and can provide a reduction in rib-induced artifacts.

The inventors have appreciated that conventional coherence imaging as applied to ultrasound devices, whether used for cardiac imaging or otherwise, suffers from its own drawbacks. A primary drawback of conventional coherence imaging in ultrasound devices is the computation-intensive nature of the technique. Performing an auto-correlation is computationally intensive, particularly when the ultrasound imaging device includes a large number of ultrasonic transducers producing a large number of received signals in response to receiving ultrasound energy. The auto-correlation function involves the performance of multiplication operations for signals received from a given ultrasonic transducer with those received from all other ultrasonic transducers of the ultrasound imaging device. The larger the number of ultrasonic transducers, the greater the computational complexity.

Accordingly, the inventors have developed techniques for ultrasound imaging that utilize an approximation of auto-correlation of ultrasound signals received at different ultrasonic transducer elements, thus allowing for improved coherence imaging to be performed. The techniques described herein result in faster and less resource-intensive coherence imaging compared to auto-correlation processing in conventional coherence imaging.

In some embodiments, a method is provided that performs coherence imaging. The method may approximate auto-correlation of received ultrasound signals from ultrasonic transducer elements without any auto-correlation calculation, and determine the output image based on the approximation. In approximating the auto-correlation, the method may group the ultrasound signals into multiple portions, each corresponding to a respective sub-aperture of a plurality of sub-apertures. The method may determine a coherent sum of signals for each sub-aperture, perform a processing operation over the coherent sum to obtain resulting data. For example, the processing operation may be a square or a magnitude square (in case of a complex value) of the coherent sum. The method may normalize the processed coherent sum for each sub-aperture by the incoherent sums of the received ultrasound signals associated with the sub-aperture to obtain respective normalized resulting data for the sub-aperture, and sum the resulting data for all of the sub-apertures to generate the output image.

In some embodiments, a system is provided that performs coherence imaging. The system may include an ultrasonic transducer array configured to transmit ultrasound signals associated with a plurality of transducer elements and receive ultrasound signals reflected through a target tissue. Each of the received ultrasound signals may be applied with a respective delay. The system may include one or more processing devices that generate an output ultrasound image by processing the received ultrasound signals. The one or more processing devices may approximate auto-correlation of received ultrasound signals from ultrasonic transducer elements without any auto-correlation calculation, and determine the output image based on the approximation. In approximating the auto-correlation, the one or more processing devices may group the ultrasound signals into multiple portions, each corresponding to a respective sub-aperture of a plurality of sub-apertures. The one or more processing devices may determine a coherent sum of signals for each sub-aperture, perform a processing operation over the coherent sum to obtain resulting data. For example, the processing operation may be a square or a magnitude square (in case of a complex values) of the coherent sum. The one or more processing devices may normalize the processed coherent sum for each sub-aperture by the incoherent sums of the received ultrasound signals associated with the sub-aperture to obtain respective normalized resulting data for the sub-aperture, and sum the resulting data for all of the sub-apertures to generate the output image.

The coherence imaging techniques described in the present disclosure provide various advantages over conventional coherence imaging systems. In addition to the saving of computing resource that results from the approximation of auto-correlation of ultrasound signals, the systems and methods also provide various degrees of freedom, including control of the desired lags, lateral resolution, and speckle content of the image through suitable choice of sub-aperture size, number, and degree of overlap. As a result, in vivo improvements in cardiac contrast resolution can be achieved. This improvement in cardiac contrast resolution may be particularly desirable in imaging a subject whose organs (e.g., large lungs or fat layers) may cause the ultrasound image to contain "clutter," which tends to effectively reduces contrast resolution of the image. Thus, the coherence imaging techniques provided herein may reduce the noise and improve contrast resolution in imaging tissues of different patient types.

The aspects and embodiments described above, as well as additional aspects and embodiments, are described further below. These aspects and/or embodiments may be used individually, all together, or in any combination of two or more, as the application is not limited in this respect.

FIG. 1A is a block diagram of an example of an ultrasound device in accordance with some embodiments of the technology described herein. The illustrated ultrasound device may implement the signal processing techniques described herein, including the coherence imaging techniques described herein. The illustrated ultrasound device 100 may include one or more ultrasonic transducer arrangements (e.g., arrays) 102, transmit (TX) circuitry 104, receive (RX) circuitry 106, a timing and control circuit 108, a signal conditioning/processing circuit 110, a power management circuit 118, and/or a high-intensity focused ultrasound (HIFU) controller 120. Additionally, the ultrasound device 100 may include a beamformer controller 122, transmit (TX) beamformer 124, receive (RX) beamformer 126, and auto-correlation approximation circuitry 128.

The one or more ultrasonic transducer arrays 102 may take on any of numerous forms, and aspects of the present technology do not necessarily require the use of any particular type or arrangement of ultrasonic transducer cells or ultrasonic transducer elements. For example, multiple ultrasonic transducer elements in the ultrasonic transducer array 102 may be arranged in one-dimension, or two-dimensions. Although the term "array" is used in this description, it should be appreciated that in some embodiments the ultrasonic transducer elements may be organized in a non-array fashion. In various embodiments, each of the ultrasonic transducer elements in the array 102 may, for example, include one or more capacitive micromachined ultrasonic transducers (CMUTs), one or more CMOS ultrasonic transducers (CUTs), or one or more piezoelectric micromachined ultrasonic transducers (PMUTs).

In some embodiments, the TX circuitry 104 may, for example, generate pulses that drive the individual elements of, or one or more groups of elements within, the ultrasonic transducer array(s) 102 so as to generate acoustic signals to be used for imaging. The RX circuitry 106, on the other hand, may receive and process electronic signals generated by the individual elements of the ultrasonic transducer array(s) 102 when acoustic signals impinge upon such elements.

As described above, in some embodiments, ultrasound device 100 may include beamformer components configured to perform beamforming, such as beamformer controller 122, a Tx beamformer 124, and a Rx beamformer 126. An auto-correlation approximation circuitry 128 may also be included, and may contribute to the beamforming functionality. The beamformer controller 122 may be coupled to the Tx beamformer 124 and the Rx beamformer 126 to control beamforming in the ultrasound device 100. For example, the Tx beamformer and the Rx beamformer may be coupled to the Tx circuitry 104 and the Rx circuitry 106, respectively. Accordingly, the Tx circuitry 104 and the Rx circuitry 106 may be configured to perform beamforming. The beamforming may obtain ultrasound signals reflected from a tissue, where the ultrasound signals are received by each ultrasonic transducer element with an appropriate delay applied as configured by the beamformer components, depending on the ultrasonic transducer element, the pixel of interest in the tissue, and other factors. In some embodiments, the beamformer controller 122 may be coupled to the auto-correlation approximation circuitry 128 to generate ultrasound data from the received ultrasound signals using coherence imaging principle.

In some embodiments, the auto-correlation approximation circuitry 128 may be configured to perform coherence imaging without any auto-correlation calculation. In some examples, for a point in a target tissue, the auto-correlation approximation circuitry 128 may group the received ultrasound signals into a plurality of portions, each portion associated with a respective one of a plurality of sub-apertures of the ultrasonic transducer array. A sub-aperture may include a subset of ultrasonic transducer elements in the ultrasonic transducer array. In some embodiments, the plurality of sub-apertures may overlap with each other. For a plurality (and in some cases, each) of the plurality of sub-apertures, the auto-correlation approximation circuitry 128 may determine a respective coherent sum over a respective portion of the received signals associated with the sub-aperture; perform a processing operation over the respective coherent sum to obtain respective resulting data; and sum the resulting data for the plurality of sub-apertures for imaging the tissue.

In some examples, the processing operation as applied to a coherent sum may involve computing the magnitude square of complex values in the coherent sum. By computing the magnitude square of a coherent sum, cross-multiplications of the terms in the coherent sum (as needed in obtaining auto-correlation of the signals) may be automatically obtained without calculating the cross-multiplications themselves. Thus, an approximation of auto-correlation of ultrasound signals may be achieved based on taking the magnitude square (or square) of the coherent sum for each of the sub-apertures and summing these magnitude squares (or squares), followed by a normalizing operation using the incoherent sum of the ultrasound signals in each sub-aperture. Such an approximation may provide coherence imaging results. Accordingly, the computations required of calculating the auto-correlation can be avoided, meaning the desired results may be obtained with meaningfully fewer computational resources. Details of the auto-correlation approximation circuitry 128 will be further described with reference to FIGS. 2-5.

With further reference to FIG. 1A, in some embodiments, the timing and control circuit 108 may be, for example, responsible for generating all timing and control signals that are used to synchronize and coordinate the operation of the other elements in the device 100. In the example shown, the timing and control circuit 108 is driven by a single clock signal CLK supplied to an input port 116. The clock signal CLK may be, for example, a high-frequency clock used to drive one or more of the on-chip circuit components. In some embodiments, the clock signal CLK may, for example, be a 1.5625 GHz or 2.5 GHz clock used to drive a high-speed serial output device (not shown in FIG. 1A) in the signal conditioning/processing circuit 110, or a 20 Mhz or 40 MHz clock used to drive other digital components on the die 112, and the timing and control circuit 108 may divide or multiply the clock CLK, as necessary, to drive other components on the die 112. In other embodiments, two or more clocks of different frequencies (such as those referenced above) may be separately supplied to the timing and control circuit 108 from an off-chip source. In some embodiments, the output range of a same (or single) transducer unit in an ultrasound device may be anywhere in a range of 1-12 MHz (including the entire frequency range from 1-12 MHz), making it a universal solution, in which there is no need to change the ultrasound heads or units for different operating ranges or to image at different depths within a patient. That is, the transmit and/or receive frequency of the transducers of the ultrasonic transducer array may be selected to be any frequency or range of frequencies within the range of 1 MHz-12 MHz, allowing for a single ultrasound transducer array to operate across frequency ranges which might otherwise require multiple separate transducer arrays. For cardiac imaging applications, frequencies between 1 MHz-5 MHz may be used. Therefore, in some embodiments of the present application, a handheld ultrasound probe is provided, configured to perform cardiac ultrasound imaging and having an ultrasonic transducer array configured to selectively transmit ultrasound signals at frequencies between 1 MHz and 5 MHz.

The power management circuit 118 may be, for example, responsible for converting one or more input voltages $V_{IN}$ from an off-chip source into voltages needed to carry out operation of the chip, and for otherwise managing power consumption within the device 100. In some embodiments, for example, a single voltage (e.g., 12V, 80V, 100V, 120V, etc.) may be supplied to the chip and the power management circuit 118 may step that voltage up or down, as necessary, using a charge pump circuit or via some other DC-to-DC voltage conversion mechanism. In other embodiments, multiple different voltages may be supplied separately to the power management circuit 118 for processing and/or distribution to the other on-chip components.

In the embodiment shown above, all of the illustrated elements are formed on a single semiconductor die 112. It should be appreciated, however, that in alternative embodiments one or more of the illustrated elements may be instead located off-chip, in a separate semiconductor die, or in a separate device. For example, the beamformer components, e.g., beamformer controller 122, Tx beamformer 124, Rx beamformer 126, and/or auto-correlation approximation circuitry 128 may be implemented inside the same semiconductor die 112. Alternatively, one or more of these components may be implemented in a DSP chip, a field programmable gate array (FPGA) in a separate chip, or a separate application specific integrated circuity (ASIC) chip. Additionally, and/or alternatively, one or more of the components in the beamformer may be implemented in the semiconductor die 112, whereas other components in the beamformer may be implemented in an external processing device in hardware or software, where the external processing device is capable of communicating with the ultrasound device 100.

In addition, although the illustrated example shows both TX circuitry 104 and RX circuitry 106, in alternative embodiments only TX circuitry or only RX circuitry may be employed. For example, such embodiments may be employed in a circumstance where one or more transmission-only devices are used to transmit acoustic signals and one or more reception-only devices are used to receive acoustic signals that have been transmitted through or reflected off of a subject being ultrasonically imaged.

It should be appreciated that communication between one or more of the illustrated components may be performed in any of numerous ways. In some embodiments, for example, one or more high-speed busses (not shown), such as that employed by a unified Northbridge, may be used to allow high-speed intra-chip communication or communication with one or more off-chip components.

Figure 10:
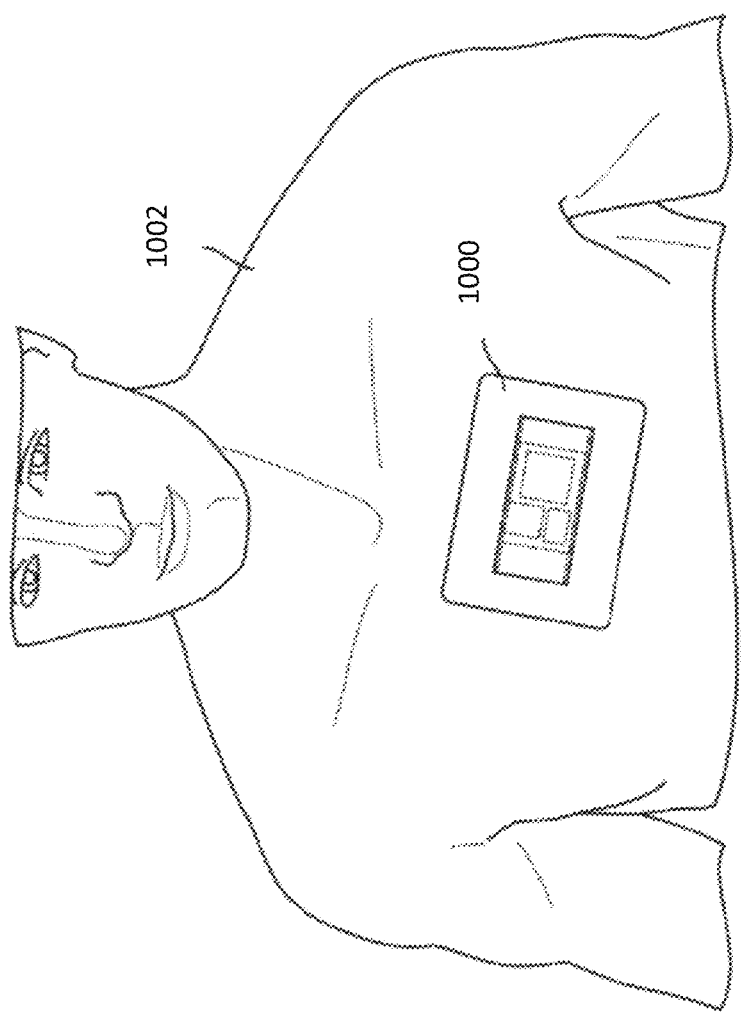
FIG. 10 illustrates an example wearable ultrasound patch, in accordance with certain embodiments described herein.
Figure 11:
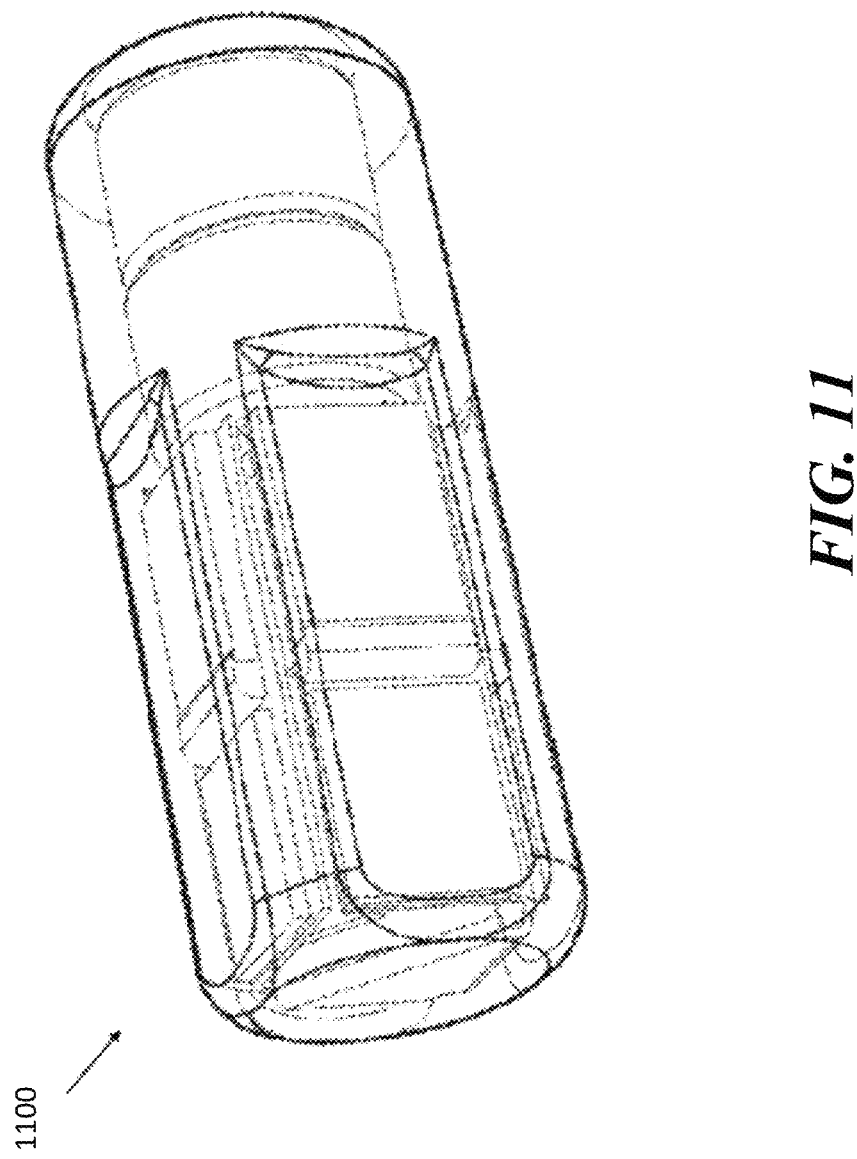
FIG. 11 illustrates an example ingestible ultrasound pill, in accordance with certain embodiments described herein.

In some embodiments, the ultrasonic transducer elements of the ultrasonic transducer array 102 may be formed on the same chip as the electronics of the TX circuitry 104 and/or RX circuitry 106. The ultrasonic transducer arrays 102, TX circuitry 104, and RX circuitry 106 may be, in some embodiments, integrated in a single ultrasound probe. In some embodiments, the single ultrasound probe may be a hand-held probe including, but not limited to, the hand-held probes described below with reference to FIG. 9. In other embodiments, the single ultrasound probe may be embodied in a patch that may be coupled to a patient. FIG. 10 provides a non-limiting illustration of such a patch. The patch may be configured to transmit, wirelessly, data collected by the patch to one or more external devices for further processing. In other embodiments, the single ultrasound probe may be embodied in a pill that may be swallowed by a patient. The pill may be configured to transmit, wirelessly, data collected by the ultrasound probe within the pill to one or more external devices for further processing. FIG. 11 illustrates a non-limiting example of such a pill.

A CUT may include, for example, a cavity formed in a CMOS wafer, with a membrane overlying the cavity, and in some embodiments sealing the cavity. Electrodes may be provided to create an ultrasonic transducer cell from the covered cavity structure. The CMOS wafer may include integrated circuitry to which the ultrasonic transducer cell may be connected. The ultrasonic transducer cell and CMOS wafer may be monolithically integrated, thus forming an integrated ultrasonic transducer cell and integrated circuit on a single substrate (the CMOS wafer).

As shown in FIG. 1A, in some embodiments, a HIFU controller 120 may be integrated on the die 112 so as to enable the generation of HIFU signals via one or more elements of the ultrasonic transducer array(s) 102. In other embodiments, a HIFU controller for driving the ultrasonic transducer array(s) 102 may be located off-chip, or even within a device separate from the device 100. That is, aspects of the present disclosure relate to provision of ultrasound-on-a-chip HIFU systems, with and without ultrasound imaging capability. It should be appreciated, however, that some embodiments may not have any HIFU capabilities and thus may not include a HIFU controller 120.

Moreover, it should be appreciated that the HIFU controller 120 may not represent distinct circuitry in those embodiments providing HIFU functionality. For example, in some embodiments, the remaining circuitry of FIG. 1A (other than the HIFU controller 120) may be suitable to provide ultrasound imaging functionality and/or HIFU, i.e., in some embodiments the same shared circuitry may be operated as an imaging system and/or for HIFU. Whether or not imaging or HIFU functionality is exhibited may depend on the power provided to the system. HIFU typically operates at higher powers than ultrasound imaging. Thus, providing the system a first power level (or voltage level) appropriate for imaging applications may cause the system to operate as an imaging system, whereas providing a higher power level (or voltage level) may cause the system to operate for HIFU. Such power management may be provided by off-chip control circuitry in some embodiments.

In addition to using different power levels, imaging and HIFU applications may utilize different waveforms. Thus, waveform generation circuitry may be used to provide suitable waveforms for operating the system as either an imaging system or a HIFU system.

In some embodiments, the system may operate as both an imaging system and a HIFU system (e.g., capable of providing image-guided HIFU). In some such embodiments, the same on-chip circuitry may be utilized to provide both functions, with suitable timing sequences used to control the operation between the two modalities.

In the example shown, one or more output ports 114 may output a high-speed serial data stream generated by one or more components of the signal conditioning/processing circuit 110. Such data streams may be, for example, generated by one or more USB 3.0 modules, and/or one or more 10 GB, 40 GB, or 100 GB Ethernet modules, integrated on the die 112. It is appreciated that other communication protocols may be used for the output ports 114.

In some embodiments, the signal stream produced on output port 114 can be provided to a computer, tablet, or smartphone for the generation and/or display of two-dimensional, three-dimensional, and/or tomographic images. In some embodiments, the signal provided at the output port 114 may be ultrasound data provided by the one or more beamformer components or auto-correlation approximation circuitry 128, where the ultrasound data may be used by the computer (external to the ultrasound device) for displaying the ultrasound images. In embodiments in which image formation capabilities are incorporated in the signal conditioning/processing circuit 110, even relatively low-power devices, such as smartphones or tablets which have only a limited amount of processing power and memory available for application execution, can display images using only a serial data stream from the output port 114. As noted above, the use of on-chip analog-to-digital conversion and a high-speed serial data link to offload a digital data stream is one of the features that helps facilitate an "ultrasound on a chip" solution according to some embodiments of the technology described herein.

Figure 1B:
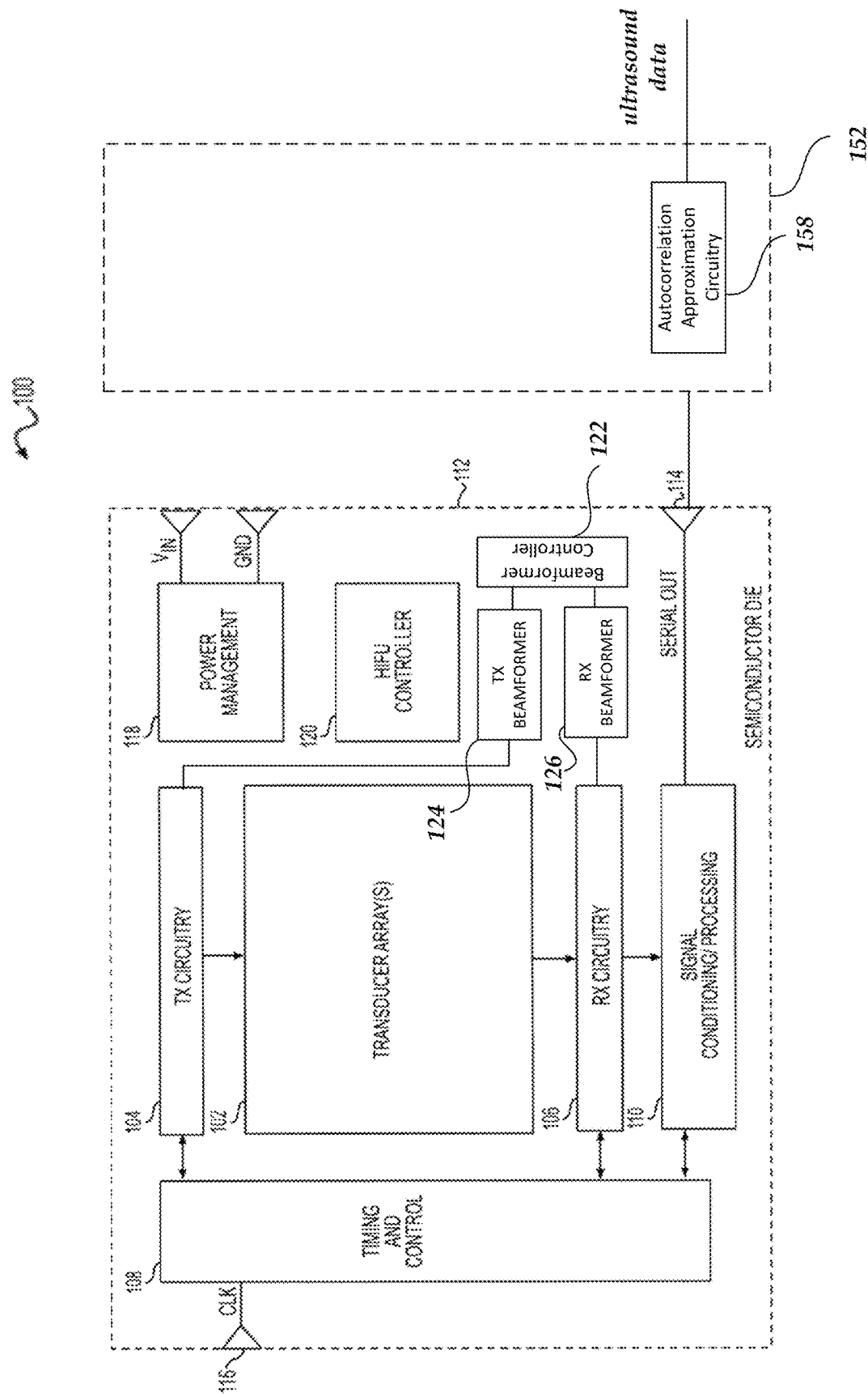
FIG. 1B is a block diagram of an example of an ultrasound device including a beamformer for performing an approximation function of a coherence imaging process that may be formed in a separate semiconductor die from the die in which the ultrasonic transducer array is located, in accordance with some embodiments of the technology described herein.

FIG. 1B is a block diagram of a variation of the ultrasound device shown in FIG. 1A. For example, one or more beamformer components, including the auto-correlation approximation circuitry 158 may be formed separately on a component 152 that is coupled to the semiconductor die 112. The component 152 may be a semiconductor die in some embodiments. The component 152 may be a field programmable gate array (FPGA) in some embodiments. Thus, the output port 114 may transmit received ultrasound signals received by the ultrasound arrays 102 to the component 152.

Figure 1C:
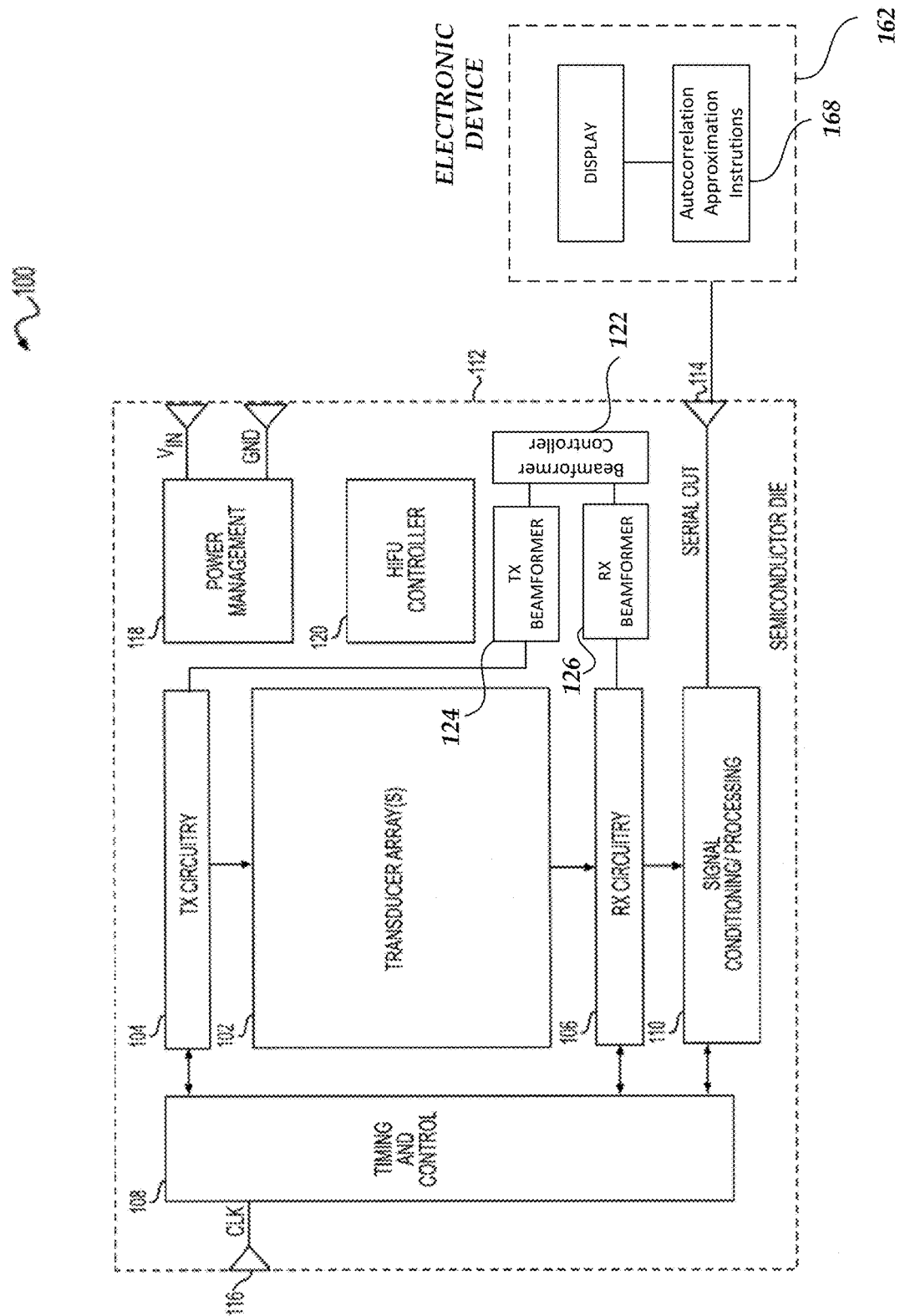
FIG. 1C is a block diagram of an example of an ultrasound device couplable to an external electronic device for performing a coherence imaging process that may be performed on the external electronic device, in accordance with some embodiments of the technology described herein.

FIG. 1C is a block diagram of a variation of the ultrasound device of FIGS. 1A and 1B. For example, programming instructions 168 for performing the auto-correlation approximation may reside off the chip, on an electronic device 162 that is external to the device 100. In such a case, the ultrasound signals may be provided to the external electronic device 162 through the output port 114. The electronic device 162 may be a portable electronic device, e.g., a phone, a tablet PC, or any other electronic devices capable of executing the programming instructions 168 and performing the auto-correlation approximation process.

Devices 100 such as that shown in FIGS. 1A-1C may be used in various imaging and/or treatment (e.g., HIFU) applications, and the particular examples described herein should not be viewed as limiting. In one illustrative implementation, for example, an imaging device including an N×M planar or substantially planar array of CMUT elements may itself be used to acquire an ultrasound image of a subject (e.g., a person's abdomen) by energizing some or all of the elements in the ultrasonic transducer array(s) 102 (either together or individually) during one or more transmit phases, and receiving and processing signals generated by some or all of the elements in the ultrasonic transducer array(s) 102 during one or more receive phases, such that during each receive phase the CMUT elements sense acoustic signals reflected by the subject. In other implementations, some of the elements in the ultrasonic transducer array(s) 102 may be used only to transmit acoustic signals and other elements in the same ultrasonic transducer array(s) 102 may be simultaneously used only to receive acoustic signals. Moreover, in some implementations, a single imaging device may include a P×Q array of individual devices, or a P×Q array of individual N×M planar arrays of CMUT elements, which components can be operated in parallel, sequentially, or according to some other timing scheme so as to allow data to be accumulated from a larger number of CMUT elements than can be embodied in a single device 100 or on a single die 112.

Figure 2:
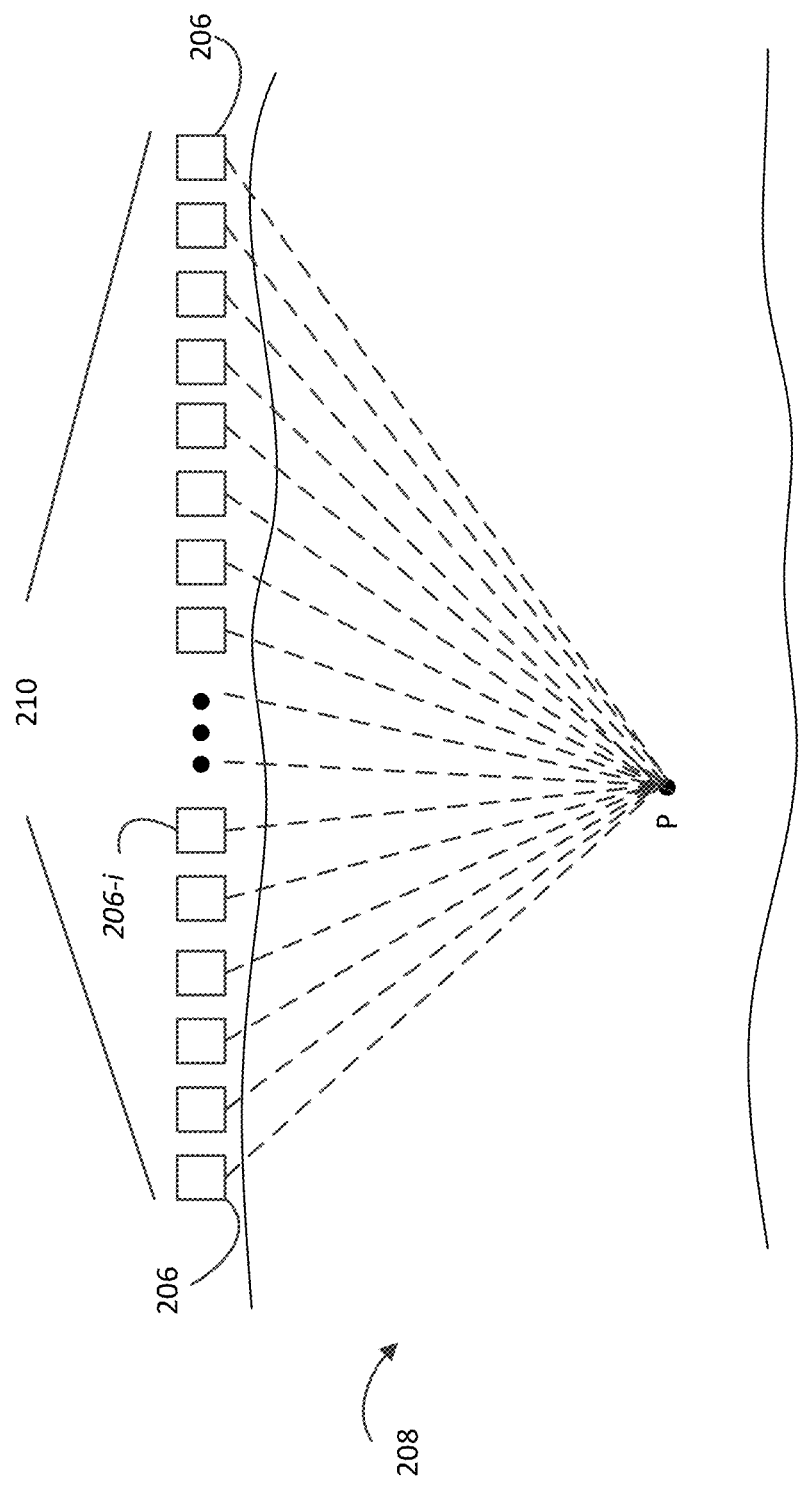
FIG. 2 illustrates a simplified ultrasonic transducer array responsible for transmitting ultrasound signals and receiving ultrasound signals reflected from a point of focus in a target tissue, in accordance with some embodiments of the technology described herein.
Figure 3:
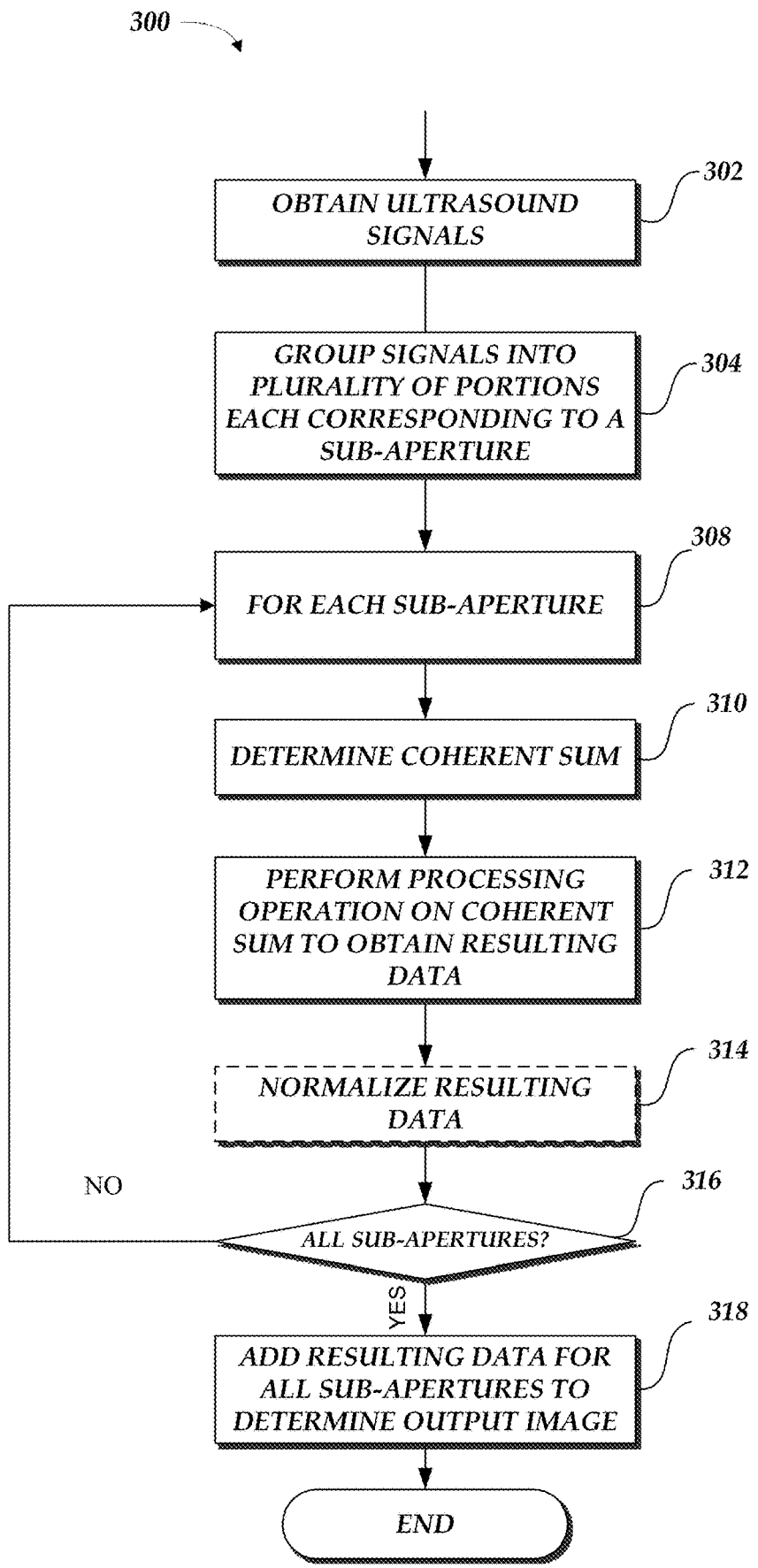
FIG. 3 is an example flow diagram of a process for performing an approximation function of a coherence imaging process in accordance with certain embodiments described herein.

With reference to FIGS. 2 and 3, the auto-correlation approximation circuitry 128, 158 (FIGS. 1A-1B) or the programming instructions for performing the auto-correlation approximation 168 of FIG. 1C are further explained. FIG. 2 illustrates a simplified ultrasonic transducer array responsible for transmitting ultrasound signals and receiving ultrasound sound signals reflected from a focused point p in a target tissue 208, in accordance with some embodiments of the technology described herein. As shown in FIG. 2, an ultrasonic transducer array 210 may include multiple ultrasonic transducer elements 206. Each ultrasonic transducer element 206 may contribute to received data for each pixel p in the tissue 208. Each of the received signals may have a respective delay, depending on the ultrasonic transducer element. Consider a point p in the tissue, and an ultrasonic transducer element e (one of the ultrasonic transducer elements 206, e.g., 206-$i$). The beamformer components in FIGS. 1A-1C may calculate the round-trip time for a transmitted pulse from element e to reach the point p, then reflect back to element e (with appropriate delay). This round-trip time may be designated $t_p(e)$. Then, at a given time, a given point p in the tissue may be represented by the ultrasound signals received from multiple ultrasonic transducer elements. In other words, as shown in FIG. 2, the plurality of ultrasonic transducer elements in the ultrasonic transducer array may simultaneously contribute some data relating to a given point p in the tissue (with appropriate delay). For example, at time $t_p(e)$, the received ultrasound signals representing a pixel p may be expressed by a vector Vp(e) containing multiple vector elements, each associated with a signal received at a respective ultrasonic transducer element e. A vector element in the vector Vp(e) may have a complex value, in some embodiments. The auto-correlation approximation circuitry (e.g., 128 in FIG. 1A, 158 in FIG. 1B) or programming instructions 168 in FIG. 1C may process the received ultrasound signals to generate ultrasound data, the details of which are further described in FIG. 3.

FIG. 3 is an example flow diagram of a process for performing an approximation function of a coherence imaging process in accordance with certain embodiments described herein. In some embodiments, method 300 may be implemented in a beamformer component, e.g., using circuitry such as auto-correlation approximation circuity 128 of FIG. 1A, 158 in FIG. 1B, or in programming instructions 168 in FIG. 1C. As described above, the auto-correlation approximation circuitry 128, 168 (FIGS. 1A and 1B) may be implemented inside an ultrasound probe. In some embodiments, the auto-correlation approximation circuitry may be implemented in a DSP chip, an FPGA, or an ASIC chip. The auto-correlation approximation circuitry may be implemented in the same semiconductor die as the transducer array. In some embodiments, the auto-correlation approximation circuitry may be implemented in a different semiconductor die or in a processing device external to the ultrasound device 100. For example, the auto-correlation approximation circuitry may be implemented in a processing device 162 of FIG. 1C configured to be communicatively coupled to the ultrasound device 100. In some embodiments, the programming instructions 168 for performing the auto-correlation approximation may be stored in a non-transitory computer readable medium. In other embodiments, the programming instructions for performing the auto-correlation approximation may be formed in a DSP chip, an FPGA, or an ASIC chip installed inside the electronic device 162. The processing device may be a dedicated computer for ultrasound imaging, in some embodiments.

In some embodiments, method 300 may include obtaining ultrasound signals at act 302. The ultrasound signals may be received from the ultrasonic transducer array, where the ultrasound signals may be reflected from transmitted beams from a plurality of ultrasonic transducer elements in the ultrasonic transducer array (e.g., 102 in FIGS. 1A-1C) through the target tissue. As described above, for a given point in the target tissue, the received ultrasound signals may include signals from the plurality of ultrasonic transducer elements, where the signals for each of the ultrasonic transducer elements may have a respective delay. For each point in the target tissue, method 300 may generate an approximation of an auto-correlation of the received signals without performing any correlation operation, and determine an image of the target tissue based in part on the approximated correlation of the received signals. The operation of approximating the auto-correlation of the received ultrasound signals is further explained below.

In some embodiments, method 300 may group the ultrasound signals into a plurality of portions at act 304, where each portion may correspond to a respective one of a plurality of sub-apertures of the ultrasonic transducer array.

Figure 4A:
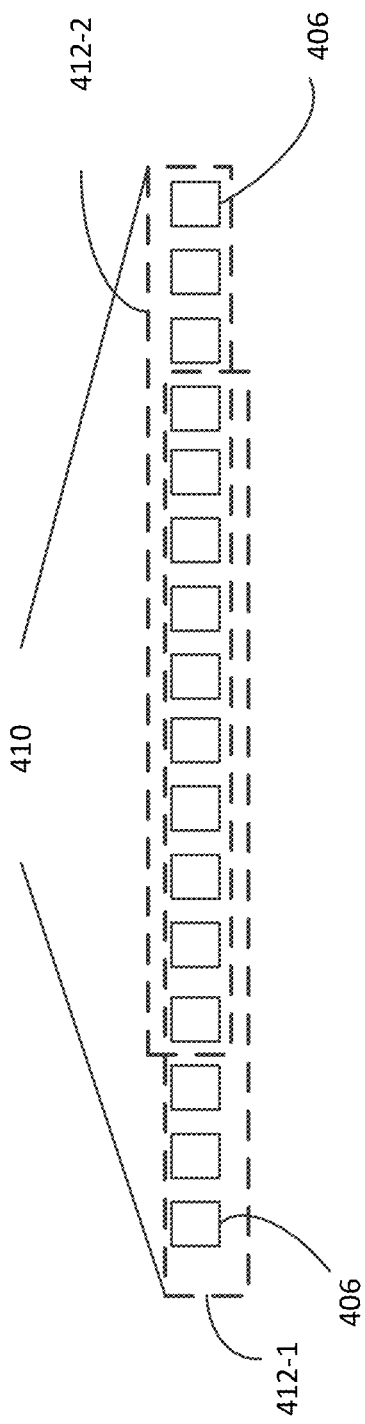
FIG. 4A illustrates an example arrangement of two overlapping sub-apertures of an ultrasonic transducer array, in accordance with some embodiments of the technology described herein.

A sub-aperture may include a subset of ultrasonic transducer elements in the transducer array. For example, FIG. 4A shows an example arrangement of two overlapping sub-apertures of an ultrasonic transducer array, where each sub-aperture corresponds to a portion of received ultrasound signal in performing coherence imaging, in accordance with some embodiments of the technology described herein. As shown in FIG. 4A, the ultrasonic transducer elements 406 in the full aperture 410 may be grouped into two overlapping sub-apertures 412-1, 412-2. Each of the sub-apertures 412-1, 412-2 may include multiple ultrasonic transducer elements 406. Accordingly, the received ultrasound signals representing a point p in the target tissue, e.g., Vp(e) may be grouped in two portions, $Vp(e)_1$ and $Vp(e)_2$ each corresponding to the sub-apertures 412-1, 412-2, respectively. As shown in FIG. 4A, sub-apertures 412-1 and 412-2 are overlapped with each other. In other words, the sub-apertures 412-1 and 412-2 may have one or more common ultrasonic transducers elements. Correspondingly, the portions of ultrasound signals $Vp(e)_1$ and $Vp(e)_2$ may also have common data that belong to both portions.

Figure 4B:
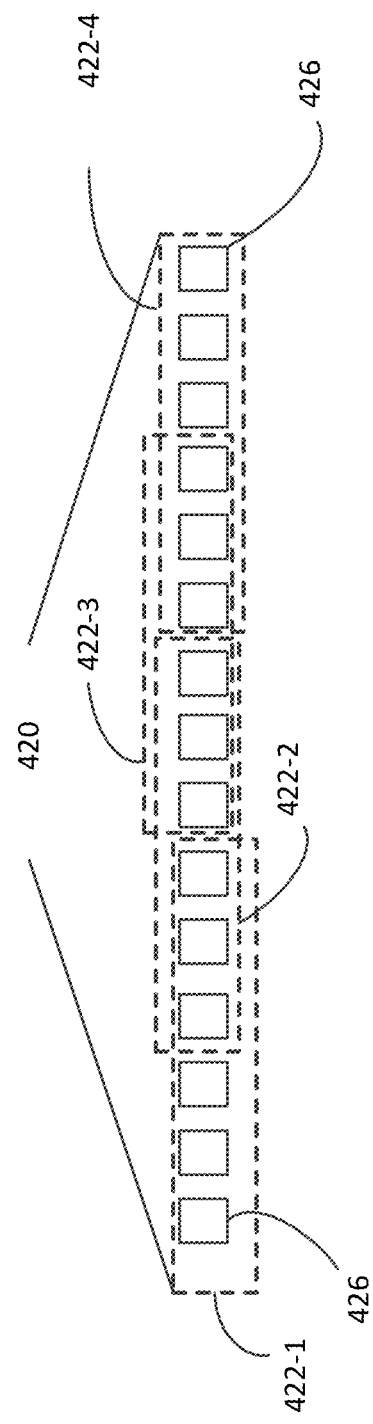
FIG. 4B illustrates an example arrangement of four overlapping sub-apertures of an ultrasonic transducer array, in accordance with some embodiments of the technology described herein.

FIG. 4B shows another example arrangement of sub-aperture configurations of an ultrasonic transducer array. In this example, four overlapping sub-apertures of an ultrasonic transducer array are shown, where each sub-aperture corresponds to a portion of received ultrasound signal in performing coherence imaging, in accordance with some embodiments of the technology described herein. As shown in FIG. 4B, the ultrasonic transducer elements 426 in the full aperture 420 may be grouped into four sub-apertures (e.g., 422-1 to 422-4) each having one or more ultrasonic transducer elements 426. Correspondingly, the received ultrasound signals may be divided into four portions, each corresponding to a respective sub-aperture of the sub-apertures 422-1 to 422-4.

Returning to FIG. 3, in some embodiments, at act 304, the received ultrasound signals may be grouped into any suitable number of portions. For example, a full aperture may include 140 ultrasonic transducer elements. In a configuration having two sub-apertures, each sub-aperture may have 105 elements (75% of the full aperture), with the first sub-aperture containing 1-105 elements, and the second sub-aperture containing elements 35-140. It is appreciated that the size of each sub-aperture may be of any suitable percentage relative to the full aperture size. For example, the size of a sub-aperture may be 50%-80% of the full aperture size. The size of the sub-aperture may be higher than 80%, e.g., 90%, 95%, or 100%.

It should also be appreciated that any suitable number of sub-apertures may be possible. In some embodiments, the number of sub-apertures may be two to four, or higher. In some embodiments, the multiple sub-apertures may be arranged along the aperture in any suitable manner. For example, in a configuration having four sub-apertures, the sub-apertures may be arranged so that their centers are equally spaced along the aperture. In some embodiments, the grouping of the plurality of portions of the ultrasound signals may correspond to the grouping of ultrasonic transducer elements into the plurality of sub-apertures. For example, the number of plurality of portions of the ultrasound signals may be the same as the number of sub-apertures. Similarly, each grouped portion of the ultrasound signals may correspond to a respective sub-aperture along the full aperture.

It is noted that the sub-apertures shown in FIGS. 4A and 4B represent differing manners in which the ultrasound signals may be grouped into multiple portions for subsequent processing. However, the groupings of sub-apertures, as shown in FIGS. 4A and 4B, are not intended to limit any physical arrangement of the ultrasonic transducer elements in acquiring the ultrasound signals. For example, the ultrasound signals may be acquired by activating a subset of ultrasonic transducer elements or the full aperture in any suitable manner that is unrelated to, or independent from the manner in which the received ultrasound signals are grouped in method 300.

With continued reference to FIG. 3, method 300 may process the plurality of portions of the ultrasound signals, where each portion may correspond to a respective sub-aperture of a plurality of sub-apertures as described above. In some embodiments, method 300 may, for each sub-aperture (308), determine a respective coherent sum at act 310 over the portion of the received signals associated with the sub-aperture; and perform a processing operation over the coherent sum to obtain resulting data at act 312. Additionally, method 300 may normalize the processed coherent sum obtained from act 312 to obtain a normalized coherent sum at act 314. The operations in acts 310-314 are further explained in detail.

At time $t_p(e)$, the received ultrasound signals representing a pixel p may be expressed by a vector Vp(e) containing multiple vector elements, each representing an ultrasound signal received at a respective ultrasonic transducer element e. The coherent sum for each sub-aperture may be calculated by:

$$I_s^{coh}(p) = \sum_{i \, in \, s} V_i(t_p) \qquad \text{Eq. (1)}$$

where s stands for a given sub-aperture, $Vi(t_p)$ represents the received ultrasound signal at ultrasonic transducer element i in the sub-aperture. In some embodiments, a vector element in the vector Vp(e) may have a complex value.

In some embodiments, at act 312, method 300 may perform a processing operation over the coherent sum to obtain resulting data. For example, the processing operation may be a detection operation that performs a square operation (or magnitude square operation) over the coherent sum, and thus, the resulting data may be calculated by:

$$I_s^{coh}(p) = \left| \sum_{i \, in \, s} V_i(t_P) \right|^2 \qquad \text{Eq. (2)}$$

In case the received signals Vi(tp) have complex values, the processing operation at act 312 computes the magnitude square of the complex values in the coherent sum. In some embodiments, at act 314, method 300 may additionally normalize the processed coherent sum for each sub-aperture by the incoherent sums of the received ultrasound signals associated with the sub-aperture to obtain respective normalized resulting data for the sub-aperture, where the incoherent sum may be calculated by:

$$I_s^{incoh}(p) = \sum_{i \, in \, s} |v_i(t_P)|^2 \qquad \text{Eq. (3)}$$

With further reference to FIG. 3, method 300 may perform the acts 310-314 (for coherent sum or normalized coherent sum) iteratively for each of the sub-apertures. Once the resulting data for all of the sub-apertures are obtained (act 316), method 300 may sum the resulting data for all of the sub-apertures to obtain the final coherence imaging result at act 318. The final coherence imaging result is calculated by:

$$I_{coherence}(p) = \sum_s \left( \frac{I_s^{coh}(p)}{I_s^{incoh}(p)} \right) \qquad \text{Eq. (4)}$$

The equation above shows a sum of normalized processed coherence sum for all of the sub-apertures. This normalization may allow the system to achieve a reasonable approximation of the auto-correlation of ultrasound signals in light of double-counted cross-multiplication terms introduced from the processing operation (e.g., 312 in FIG. 3) over the coherent sums due to overlapping sub-apertures.

Although it is shown in FIG. 3 that acts 304-306 in method 300 are performed for a given point p in the target tissue, the acts in method 300 may be performed iteratively for each point in the target tissue to generate a whole ultrasound image, for example, a 2-D image. In some examples, each point in the target tissue may correspond to a pixel in the 2D ultrasound image. Accordingly, method 300 may further include determining output data for imaging the target issue at an additional point by performing the operations comprising: processing a plurality of portions of additional ultrasound signals associated with the additional point in the target tissue; and determining output data for imaging the target tissue at the additional point by summing the resulting data for the plurality of portions of the additional signals. In some embodiments, each of the plurality of portions of additional ultrasound signals is associated with a respective one of the plurality of sub-apertures of the ultrasonic transducer array. The processing of the plurality of portions of additional ultrasound signals may include: determining a respective coherent sum over each of the plurality of portions of the additional signals associated with the additional point in the target tissue; and performing the processing operation over the respective coherent sum to obtain respective resulting data for each of the plurality of portions of the additional ultrasound signals. In the example above in 2D ultrasound image, the operations in method 300 may be performed iteratively for multiple additional points in the target tissue to generate corresponding values for each of the pixels in the ultrasound image.

Although it is shown that act 318 is performed after the resulting data for all of the sub-apertures are generated, it is appreciated that the summing operation at act 318 may be performed in various ways. For example, method 300 may add resulting data to a data buffer as the resulting data for a respective sub-aperture is calculated (at act 312 or 314). Once the resulting data for all of the sub-apertures are generated, sum operation at act 318 is performed. In other variations, method 300 may perform the sum operation at act 318 recursively to an intermediate sum as the resulting data for each of the sub-apertures are generated (at act 312 or 314) and save the intermediate sum each time to a data buffer, without waiting for the ultrasound signals in all of the sub-apertures are processed. When the iteration for all of the sub-apertures is completed (318), the intermediate sum in the data buffer becomes the final result.

Figure 5A:
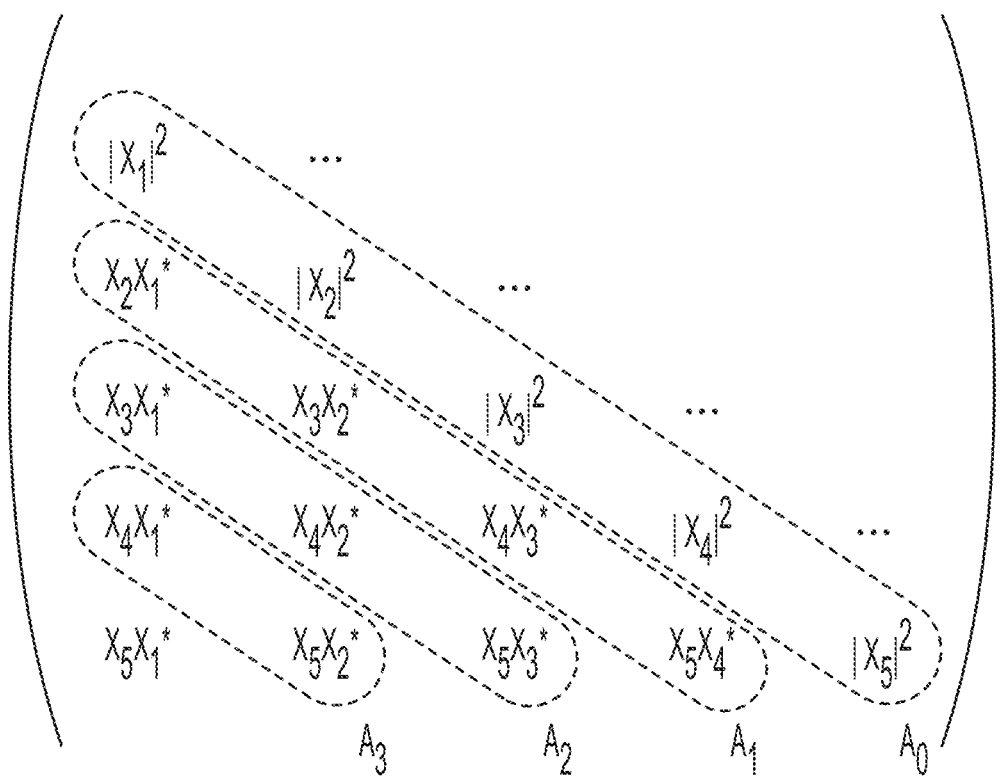
FIG. 5A illustrates a simplified covariance matrix of ultrasound signals showing the cross-multiplication terms that are required in a calculation of auto-correlation of ultrasound signals, in accordance with some embodiments of the technology described herein.

FIG. 5A illustrates a simplified covariance matrix of ultrasound signals showing the cross-multiplication terms that are required in a calculation of auto-correlation of ultrasound signals, in accordance with some embodiments of the technology described herein. A covariance matrix of ultrasound signals may show how similar every ultrasonic transducer element may be to every other ultrasonic transducer element. In the covariance matrix shown, each of the $A_i$ denotes the auto-correlation across the aperture at distance (lag) i, defined as $<x(i) x(e+i)^*>_e$ where "*" stands for a conjugate of a complex value, "| |" stands for the magnitude of a complex value, $< >_e$ represents the average over all elements e, and x(i) represents a vector element in the received ultrasound signal, e.g., Vp(e=i). As shown, each of the auto-correlations lags $A_i$ requires multiple cross-multiplication terms among the ultrasound signals received from various ultrasonic transducer elements. Considering an ultrasound probe may have hundreds of ultrasonic transducer elements, the covariance matrix may be large (e.g., 100×100), and thus, direct calculation of cross-multiplication terms may be computational extensive. In some embodiments, the cross-multiplication terms as shown in FIG. 5A do not need to be directly calculated. This is further explained with reference to FIG. 5B and FIG. 3.

Figure 5B:
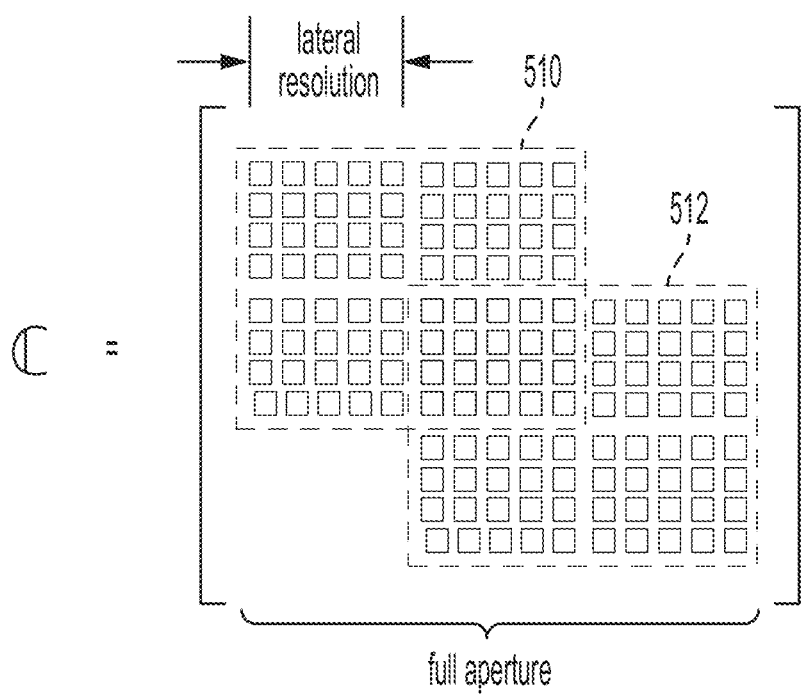
FIG. 5B illustrates a covariance matrix of received ultrasound signals as obtained by the process of FIG. 3, in accordance with some embodiments of the technology described herein.

FIG. 5B illustrates a covariance matrix of received ultrasound signals as obtained by the process of FIG. 3, in accordance with some embodiments of the technology described herein. In a simple illustration, a cross-multiplication term between two variables ab may be obtained from $(a+b)^2=a^2+b^2+2ab$. Similarly, $(a+b+c+d+\ldots)^2$ may provide the cross-multiplication terms ab, bc, cd, ac, bd, and ad etc. Referring to Eq. (2) at act 312 (FIG. 3), the processing operation applied to the coherent sum may be a square operation or a magnitude square operation. This operation effectively gives the result that evaluates the cross-multiplication terms among the vector elements used in calculating each coherent sum. Noting that the square operation or the magnitude square operation requires one single multiplication. In contrast, in conventional coherence imaging techniques, directly calculating the cross-multiplications in the auto-correlation may require $(l_0+1)(N-l_0/2)$ multiplications, where $l_0$ is the number of distances (lags) in the auto-correlation of ultrasound signals and N is the number of ultrasonic transducer elements. Accordingly, the process of FIG. 3 results in a saving of computations because direct calculation of auto-correlation of ultrasound signals is not needed.

With reference to FIG. 5B, the covariance matrix obtained by the process of FIG. 3 shows two regions 510, 512, where each element in the regions 510, 512 represents an ultrasonic transducer element. In the example, the ultrasonic transducer elements are grouped into two overlapping sub-apertures, and each of the two regions 501, 512 corresponds to a respective sub-aperture. The elements in each region represent the contribution from the respective sub-apertures, where the contribution is obtained from processing the ultrasound signals associated with the sub-aperture. The grouping of ultrasound signals into sub-apertures and the processing of ultrasound signals associated with each sub-aperture are previously described in embodiments in FIG. 3. As shown in FIG. 5B, the result as obtained by the process of FIG. 3 shows an approximation of auto-correlation of ultrasound signals at short distances (lags). The approximation result shows that components along and/or near the main diagonal axis in the covariance matrix can be obtained. The overlapping sub-apertures may introduce double counted cross-multiplication terms (e.g., the elements in the overlapped region between regions 510 and 512). These double cross-multiplication terms may be compensated by the normalization operation (e.g., act 314 of FIG. 3, Eq. (4)), which allows the system to achieve a reasonable approximation of auto-correlation in coherence imaging.

Figure 5C:
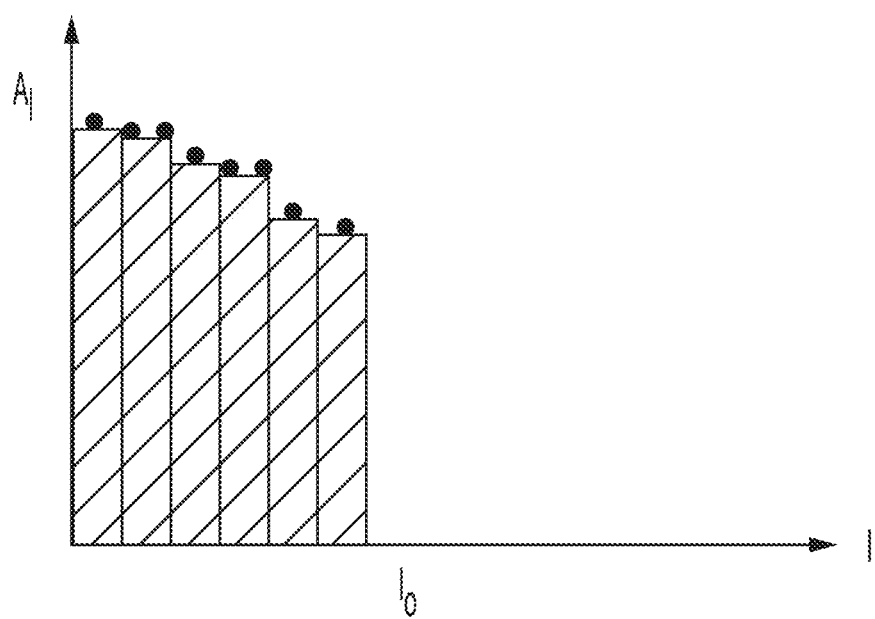
FIG. 5C illustrates an approximation of auto-correlation at short distances among the ultrasonic transducer elements as obtained by the process in FIG. 3, in accordance with some embodiments of the technology described herein.

FIG. 5C illustrates an approximation of auto-correlation at short distances (lags) among the ultrasonic transducer elements as obtained by the process in FIG. 3, in accordance with some embodiments of the technology described herein. In FIG. 5C, the results obtained by the process of FIG. 3 provides an approximation of auto-correlations at short distances (lags) in the range of $0<l<l_0$, where $l_0=n$, where n is the number of ultrasonic transducer elements in each sub-aperture. This approximation may allow the resulting ultrasound image to be close to an ultrasound image obtained by a conventional coherence imaging technique.

Various embodiments as described with reference to FIGS. 1-5C may provide advantages over conventional ultrasound imaging systems or conventional coherence imaging systems. For example, overlapping the sub-apertures may reduce the speckle noise in the ultrasound image. An example of speckle noise may include a spatial, non-uniform noisy pattern introduced by non-uniformity of the target tissue, where a system may overamplify signals reflected from a brighter portion of the tissue and suppress signals reflected from a darker portion of the tissue. Whereas conventional coherence imaging system tend to worsen the speckle noise, overlapping the sub-apertures may reduce the speckle noise in the resulting ultrasound image.

The systems and methods described above in various embodiments may be configured to suit a given ultrasound imaging application. For example, the systems and methods may provide various degrees of freedom, including control of the desired lags, lateral resolution, and speckle content of the image through suitable choice of the sub-aperture size, the number of sub-apertures, and the degree of overlap between sub-apertures. In some embodiments, the sub-aperture size may be adjusted to improve the lateral resolution in the ultrasound image. Lateral resolution may be referred to the image resolution perpendicular to the beam axis. As shown in FIG. 5B, increasing the sub-aperture size may improve the lateral resolution.

As described above, the various embodiments described herein provide advantages, such as clutter reduction, contrast enhancement and/or noise reduction. For example, in cardiac imaging, the systems and methods provided herein may suppress artifacts caused from rib interference due to the probe size. Further, more processing of received beams may be achieved with the same amount of pressure going into the target tissue. The system may also reduce the clutter by receiving reflected signals from the tissue, displaying pixels which have the same (or similar) strong return speeds and not displaying the pixels of varied low amplitude signals, for example, by using thresholding over the ultrasound data as computed using the auto-correlation approximation processed described in the present disclosure. Furthermore, the ultrasound device, as described by various embodiments may be configured to image tissues (e.g., heart) from patients in various physical sizes, such as a skinny person with small rib spaces, for which the system may be capable of fitting in between those tiny rib spaces and having a suitable pressure to penetrate for deep detail resolution.

In some embodiments, the distance (lag) in achieving the coherence imaging (e.g., $l_0$ in FIG. 5C) may be adjustable. Increasing the value of $l_0$ may improve the image resolution because higher lags in auto-correlation may result in higher spatial frequency content and also improve the overall image contrast. However, higher lags in auto-correlation may also introduce more noise because there are fewer element pairs to average across for a given lag at higher lags. As such, value of $l_0$ may be tuned based on a tradeoff between improved contrast/resolution and achieving proper signal-to-noise (SNR) ratio for the image. In some embodiments, the value of $l_0$ may be set to 1%-30% of the number of ultrasonic transducer elements in the ultrasonic transducer array. It is appreciated that the various embodiments in FIGS. 1-5C may be applied in an ultrasound system using any suitable imaging mode, such as, B-Mode, M-Mode, needle imaging, Biplane, as well as 3D B-Mode imaging.

Figure 6:
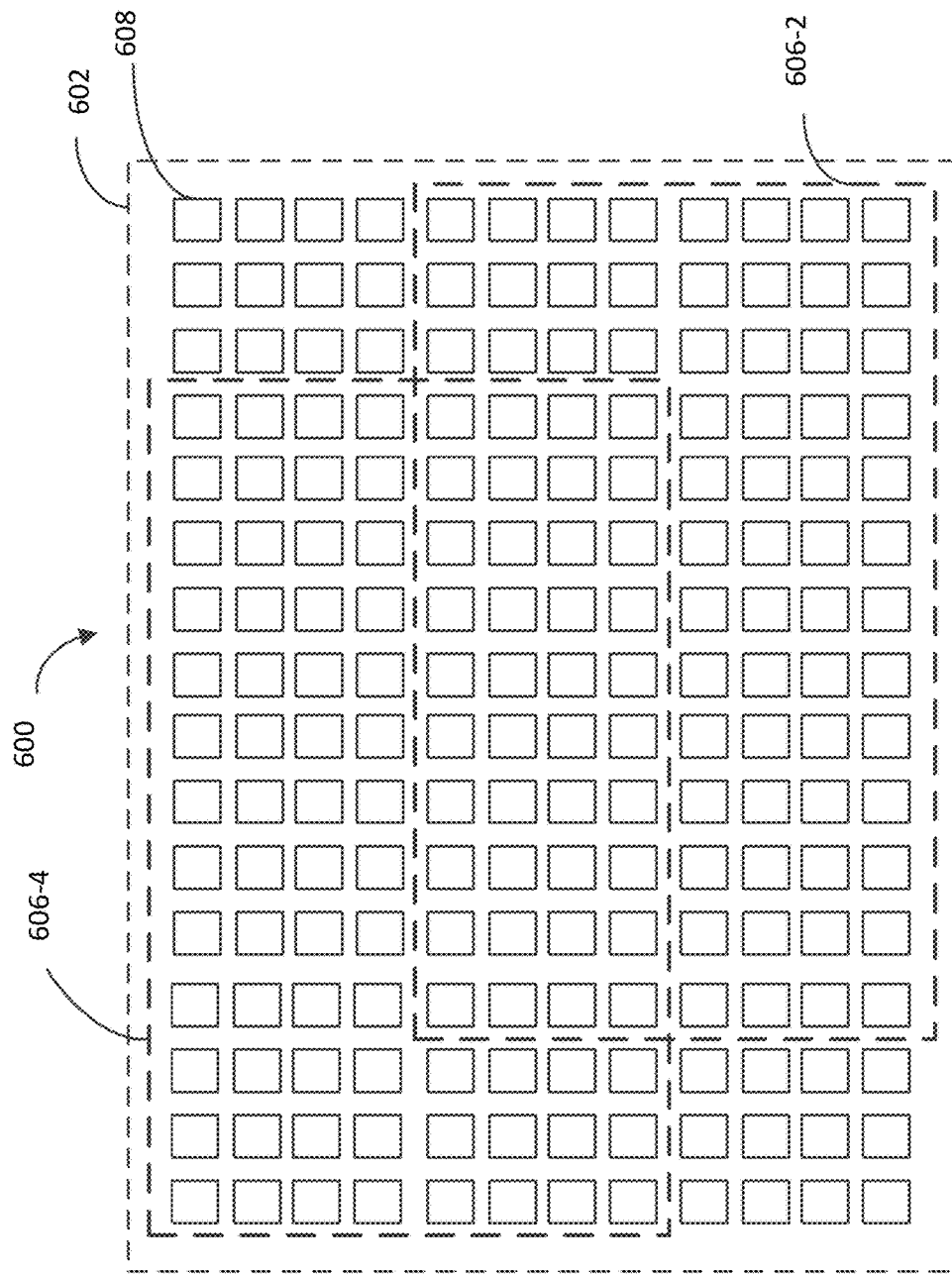
FIG. 6 shows an example two-dimensional (2D) arrangement of ultrasonic transducers with an identification of overlapping 2D sub-apertures, in accordance with some embodiments of the technology described herein.
Figure 7:
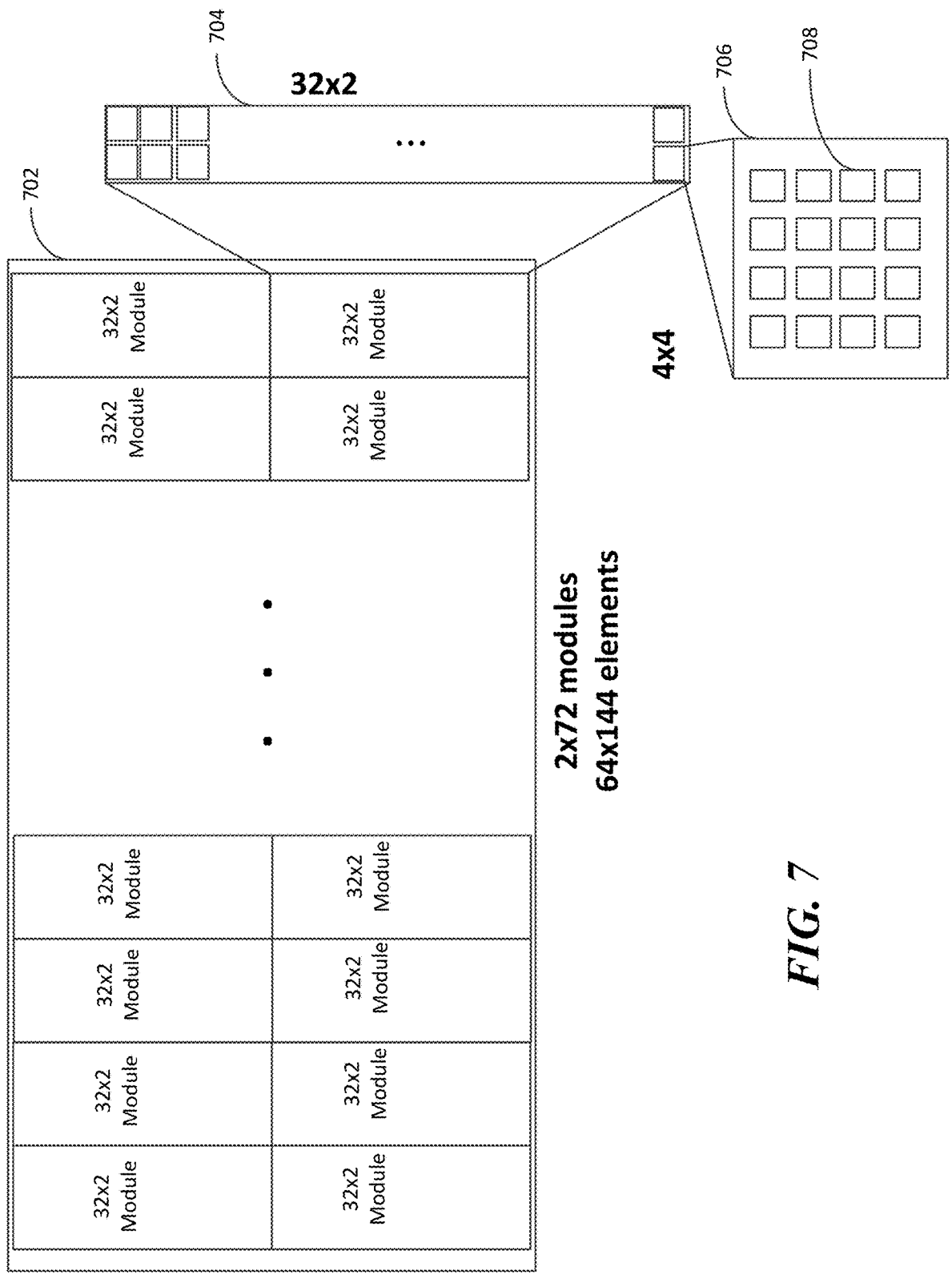
FIG. 7 shows a non-limiting example of a configuration of the arrangement of ultrasonic transducers in FIG. 6, in accordance with some embodiments of the technology described herein.

FIGS. 6 and 7 show examples of 2D ultrasonic transducer array that may implement the various embodiments described above with reference to FIGS. 1-5C. FIG. 6 shows an example 2D arrangement of ultrasonic transducer elements with an identification of overlapping 2D sub-apertures, in accordance with some embodiments of the technology described herein. In some embodiments, ultrasonic transducer array 600 may be implemented in an ultrasound device (e.g., 102 in FIGS. 1A-1C) and configured to transmit and receive ultrasound signals, which may be processed using the approximation of auto-correlation process as described in FIG. 3. As shown in FIG. 6, an ultrasonic transducer array 600 may include a plurality of ultrasonic transducer elements 608, which may be grouped into multiple overlapping sub-apertures, such as, regions 606-2 and 606-4. FIG. 7 shows a non-limiting example of a configuration of the arrangement of ultrasonic transducers in FIG. 6, in accordance with some embodiments of the technology described herein.

In some embodiments, as shown in FIG. 7, substrate 702 (e.g., a semiconductor die) of an ultrasound device may have multiple ultrasound circuitry modules 704 formed thereon. As shown, an ultrasound circuitry module 704 may comprise multiple ultrasound elements 706. An ultrasound element 706 may comprise multiple ultrasonic transducers 708, sometimes termed ultrasonic transducers.

In the illustrated embodiment, substrate 302 comprises 144 modules arranged as an array having two rows and 72 columns. However, it should be appreciated that a substrate of a single substrate ultrasound device may comprise any suitable number of ultrasound circuitry modules (e.g., at least two modules, at least ten modules, at least 100 modules, at least 1000 modules, at least 5000 modules, at least 10,000 modules, at least 25,000 modules, at least 50,000 modules, at least 100,000 modules, at least 250,000 modules, at least 500,000 modules, between two and a million modules, or any number or range of numbers within such ranges) that may be arranged as an two-dimensional array of modules having any suitable number of rows and columns or in any other suitable way.

In the illustrated embodiment, each ultrasound circuitry module 704 comprises 64 ultrasound elements arranged as an array having 32 rows and two columns. However, it should be appreciated that an ultrasound circuitry module may comprise any suitable number of ultrasound elements (e.g., one ultrasound element, at least two ultrasound elements, at least four ultrasound elements, at least eight ultrasound elements, at least 16 ultrasound elements, at least 32 ultrasound elements, at least 64 ultrasound elements, at least 128 ultrasound elements, at least 256 ultrasound elements, at least 512 ultrasound elements, between two and 1024 elements, at least 2500 elements, at least 5,000 elements, at least 10,000 elements, at least 20,000 elements, between 1000 and 20,000 elements, or any number or range of numbers within such ranges) that may be arranged as a two-dimensional array of ultrasound elements having any suitable number of rows and columns or in any other suitable way. In a non-limiting example, the ultrasound circuitry module 704 may include between approximately 6,000-10,000 (e.g., 8,960) active CMUTs on the chip, forming an array of hundreds of CMUTs by tens of CMUTs (e.g., 140×64). The CMUT element pitch may be between 150-250 um, such as 208 um, and thus, result in the total dimension of between 10-50mm by 10-50mm (e.g., 29.12 mm×13.312 mm).

In the illustrated embodiment, each ultrasound element 706 comprises 16 ultrasonic transducers 708 arranged as a two-dimensional array having four rows and four columns. However, it should be appreciated that an ultrasound element may comprise any suitable number of ultrasonic transducers (e.g., one, at least two, four, at least four, 9, at least 9, at least 16, 25, at least 25, at least 36, at least 49, at least 64, at least 81, at least 100, between one and 200, or any number or range of numbers within such ranges) that may be arranged as a two dimensional array having any suitable number of rows and columns (square or rectangular) or in any other suitable way.

It should be appreciated that any of the components described above (e.g., ultrasound transmission units, ultrasound elements, ultrasonic transducers) may be arranged as a one-dimensional array, as a two-dimensional array, or in any other suitable manner.

In some embodiments, an ultrasound circuitry module may comprise circuitry in addition to one or more ultrasound elements. For example, an ultrasound circuitry module may comprise one or more waveform generators and/or any other suitable circuitry.

In some embodiments, module interconnection circuitry may be integrated with the substrate 702 and configured to connect ultrasound circuitry modules to one another to allow data to flow among the ultrasound circuitry modules. For example, the device module interconnection circuitry may provide for connectivity among adjacent ultrasound circuitry modules. In this way, an ultrasound circuitry module may be configured to provide data to and/or receive data from one or more other ultrasound circuitry modules on the device.

Figure 8:
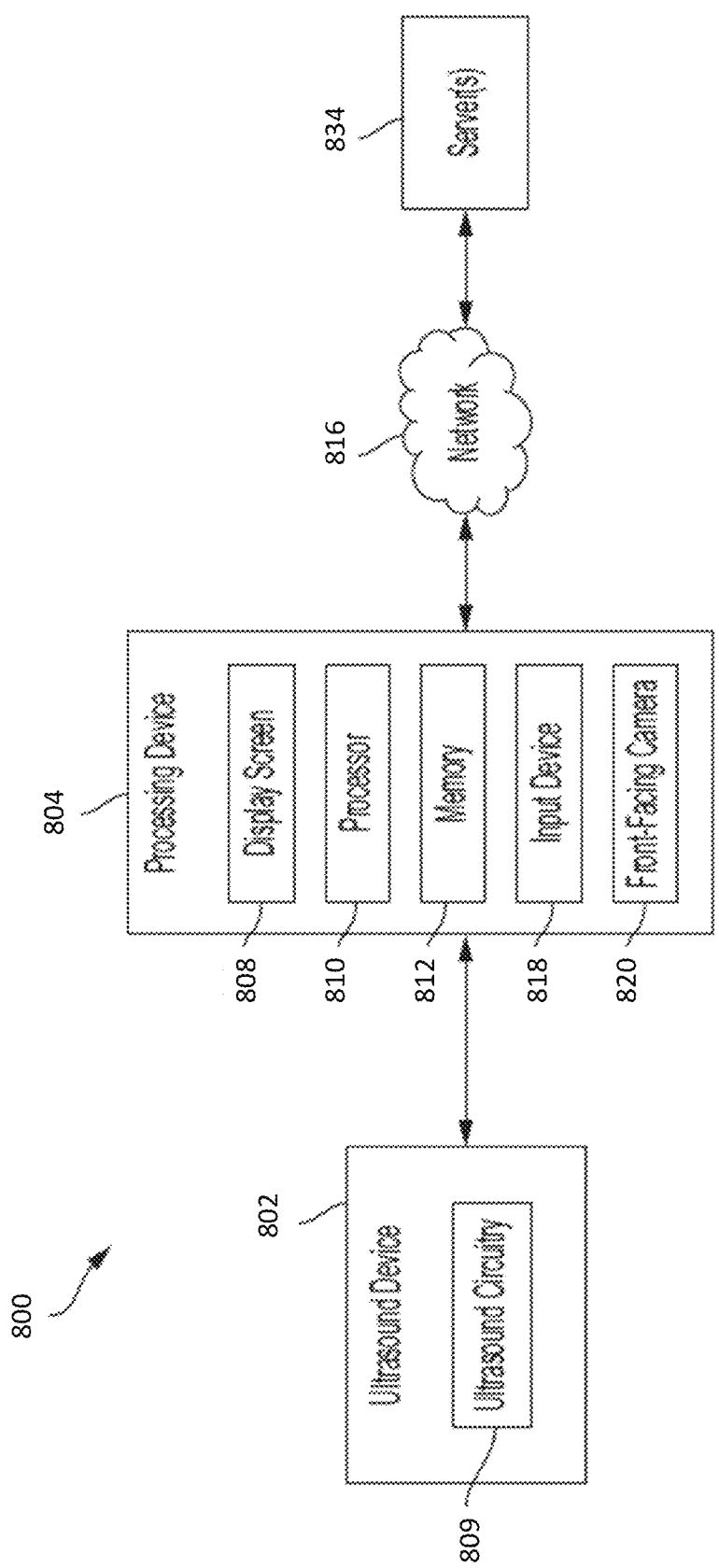
FIG. 8 illustrates a schematic block diagram of an example ultrasound system which may implement various aspects of the technology described herein.

FIG. 8 illustrates a schematic block diagram of an example ultrasound system 800 which may implement various aspects of the technology described herein. In some embodiments, ultrasound system 800 may include an ultrasound device 802, an example of which is implemented in ultrasound device 100. For example, the ultrasound device 802 may be a handheld ultrasound probe. Additionally, the ultrasound system 800 may include a processing device 804, a communication network 806, and one or more servers 808. The processing device 804 may be any of the processing devices described herein. For example, the processing device 804 may include the electronic device 162 of FIG. 1C. The ultrasound device 802 may be configured to generate ultrasound data that may be employed to generate an ultrasound image. The ultrasound device 802 may be constructed in any of a variety of ways. In some embodiments, the ultrasound device 802 includes a transmitter that transmits a signal to a transmit beamformer which in turn drives transducer elements within a transducer array to emit pulsed ultrasound signals into a structure, such as a patient. The pulsed ultrasound signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data. In some embodiments, the ultrasound device 802 may include an ultrasound circuitry 809 that may be configured to generate the ultrasound data. For example, the ultrasound device 802 may include semiconductor die 112 for implementing the various techniques described in.

Reference is now made to the processing device 804. In some embodiments, the processing device 804 may be communicatively coupled to the ultrasound device 802 (e.g., 100 in FIGS. 1A-1C) wirelessly or in a wired fashion (e.g., by a detachable cord or cable) to implement at least a portion of the process for approximating the auto-correlation of ultrasound signals. For example, one or more beamformer components (of FIGS. 1A-1C) may be implemented on the processing device 804. In some embodiments, the processing device 804 may include one or more processing devices (processors) 810, which may include specially-programmed and/or special-purpose hardware such as an ASIC chip. The processor 810 may include one or more graphics processing units (GPUs) and/or one or more tensor processing units (TPUs). TPUs may be ASICs specifically designed for machine learning (e.g., deep learning). The TPUs may be employed to, for example, accelerate the inference phase of a neural network.

In some embodiments, the processing device 804 may be configured to process the ultrasound data received from the ultrasound device 802 to generate ultrasound images for display on the display screen 808. The processing may be performed by, for example, the processor(s) 810. The processor(s) 810 may also be adapted to control the acquisition of ultrasound data with the ultrasound device 802. The ultrasound data may be processed in real-time during a scanning session as the echo signals are received. In some embodiments, the processor(s) 810 may be configured to implement the process of approximation of auto-correlation of the received ultrasound signals (e.g., method 300 in FIG. 3). In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

In some embodiments, the processing device 804 may be configured to perform the various operations described in FIG. 3, using the processor(s) 810 (e.g., one or more computer hardware processors) and one or more articles of manufacture that include non-transitory computer-readable storage media such as the memory 812. The processor(s) 810 may control writing data to and reading data from the memory 812 in any suitable manner. To perform certain of the processes described herein, the processor(s) 810 may execute one or more processor-executable instructions stored in one or more non-transitory computer-readable storage media (e.g., the memory 812), which may serve as non-transitory computer-readable storage media storing processor-executable instructions for execution by the processor(s) 810.

The camera 820 may be configured to detect light (e.g., visible light) to form an image. The camera 820 may be on the same face of the processing device 804 as the display screen 808. The display screen 808 may be configured to display images and/or videos, and may be, for example, a liquid crystal display (LCD), a plasma display, and/or an organic light emitting diode (OLED) display on the processing device 804. The input device 818 may include one or more devices capable of receiving input from a user and transmitting the input to the processor(s) 810. For example, the input device 818 may include a keyboard, a mouse, a microphone, touch-enabled sensors on the display screen 808, and/or a microphone. The display screen 808, the input device 818, the camera 820, and/or other input/output interfaces (e.g., speaker) may be communicatively coupled to the processor(s) 810 and/or under the control of the processor 810.

It should be appreciated that the processing device 804 may be implemented in any of a variety of ways. For example, the processing device 804 may be implemented as a handheld device such as a mobile smartphone or a tablet. Thereby, a user of the ultrasound device 802 may be able to operate the ultrasound device 802 with one hand and hold the processing device 804 with another hand. In other examples, the processing device 804 may be implemented as a portable device that is not a handheld device, such as a laptop. In yet other examples, the processing device 804 may be implemented as a stationary device such as a desktop computer. The processing device 804 may be connected to the network 806 over a wired connection (e.g., via an Ethernet cable) and/or a wireless connection (e.g., over a WiFi network). The processing device 804 may thereby communicate with (e.g., transmit data to or receive data from) the one or more servers 834 over the network 816. For example, a party may provide from the server 834 to the processing device 804 processor-executable instructions for storing in one or more non-transitory computer-readable storage media (e.g., the memory 812) which, when executed, may cause the processing device 804 to perform at least a portion of the process in FIG. 3. FIG. 8 should be understood to be non-limiting. For example, the ultrasound system 800 may include fewer or more components than shown and the processing device 804 and ultrasound device 802 may include fewer or more components than shown. In some embodiments, the processing device 804 may be part of the ultrasound device 802.

Figure 9:
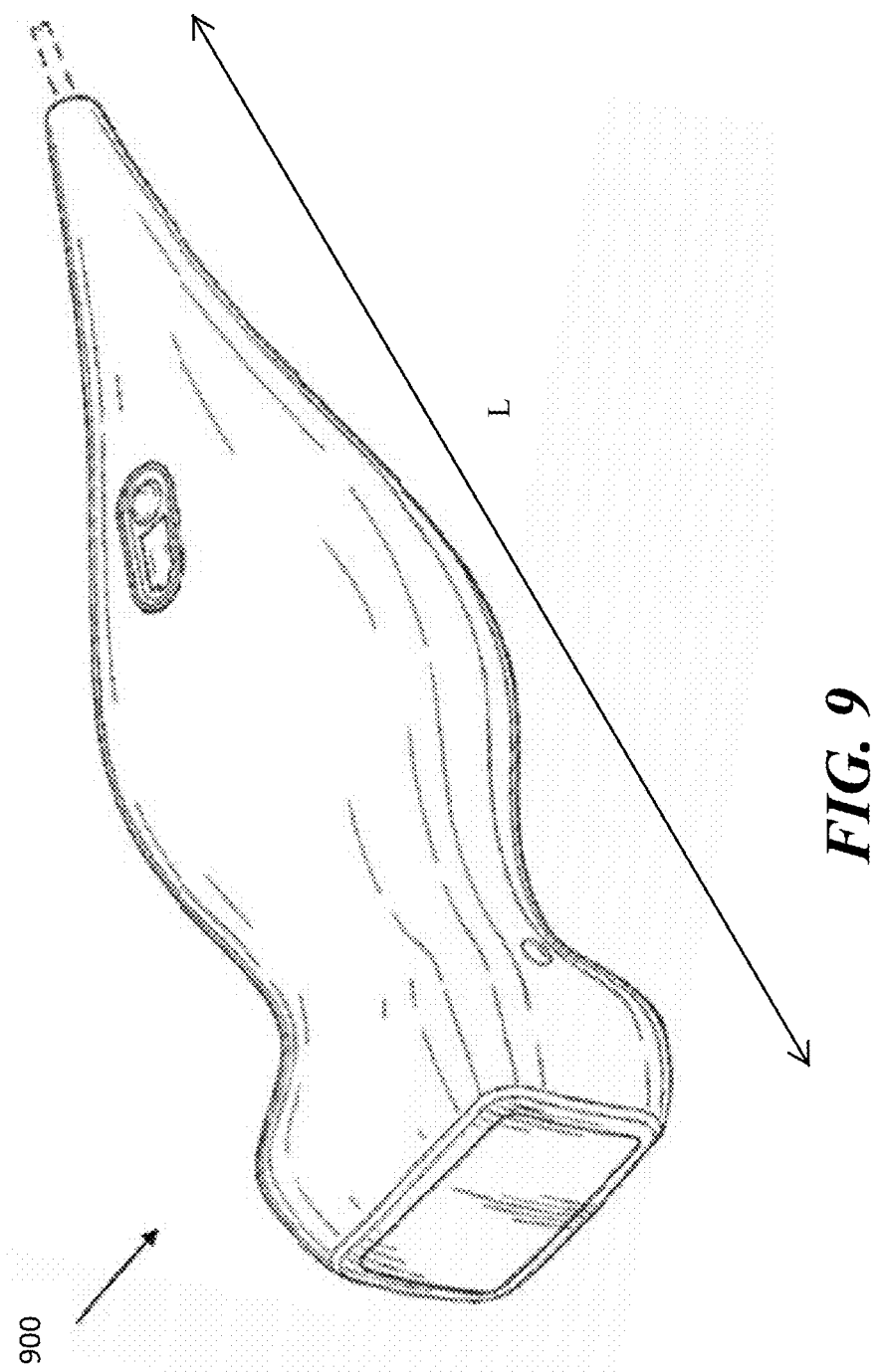
FIG. 9 illustrates an example handheld ultrasound probe, in accordance with certain embodiments described herein.

FIG. 9 illustrates an example handheld ultrasound probe, in accordance with certain embodiments described herein. Handheld ultrasound probe 900 may implement the ultrasound device 100 in FIGS. 1A-1C and/or at least a portion of the process of FIG. 3 described above. The handheld ultrasound probe 900 may be an ultrasound device, e.g., 100 (FIGS. 1A-1C), 802 (FIG. 8) operative communicative with a processing device (e.g., 804) and transmit the detected signals to the processing device. Alternatively and/or additionally, the ultrasound probe 900 may include an ultrasound device and a processing device for performing operations over ultrasound signals received from the ultrasonic transducer. In some embodiments, the handheld ultrasound probe 900 may be configured to communicate with the processing device (e.g., 804) wired or wirelessly. Thus, the handheld ultrasound probe 900 may have a suitable dimension and weight. For example, the ultrasound probe 900 may have a cable for wired communication with a processing device, and have a length L about 100 mm-300 mm (e.g., 175 mm) and a weight about 200 grams-500 grams (e.g., 312 g). In another example, the ultrasound probe 900 may be capable of communicating with a processing device wirelessly. As such, the handheld ultrasound probe 900 may have a length about 140 mm and a weight about 265 g. It is appreciated that other dimensions and weight may be possible.

FIG. 10 illustrates an example wearable ultrasound patch, in accordance with certain embodiments described herein. The wearable ultrasound patch 1000 is coupled to a subject 1002. The wearable ultrasound patch 1000 may be the same as the ultrasound device 100 (FIGS. 1A-1C), 802 (in FIG. 8) and may implement all or part of the process in FIG. 3.

FIG. 11 illustrates an example ingestible ultrasound pill, in accordance with certain embodiments described herein. The ingestible ultrasound pill 1100 may be the same as the ultrasound device 100 (FIGS. 1A-1C) or 802 (FIG. 8) and may implement all or part of the process in FIG. 3.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

The invention claimed is:

1. An apparatus, comprising:
a handheld ultrasound probe wirelessly operatively couplable to a smartphone or tablet, the handheld ultrasound probe containing:
an ultrasonic transducer array configured to selectively transmit ultrasound signals at any frequency from 1 MHz-12 MHz associated with a plurality of transducer elements and receive ultrasound signals reflected through a target tissue;
one or more processing devices configured to, for a point in the target tissue:
process a plurality of portions of received signals the point in the target tissue, wherein each of the plurality of portions is associated with grouped into a respective one of a plurality of sub-apertures of the transducer array, wherein the processing comprises:
determining a respective coherent sum over each of the plurality of portions of the received signals for each sub-aperture;
performing a processing operation over the respective coherent sum to obtain respective resulting data for each sub-aperture;
normalizing the respective resulting data for a sub-aperture of the plurality of sub-apertures by an incoherent sum of the received ultrasound signals associated with the sub-aperture; and
summing the normalized resulting data for the plurality of sub-apertures for imaging the target tissue.

2. The apparatus of claim 1, wherein the received ultrasound signals associated with the plurality of transducer elements are each delayed by a respective delay time.

3. The apparatus of claim 1, wherein the processing operation comprises at least in part a square operation or a magnitude square operation.

4. The apparatus of claim 1, wherein at least a first sub-aperture of the plurality of sub-apertures is overlapped with a second sub-aperture of the plurality of sub-apertures.

5. The apparatus of claim 4, wherein the plurality of sub-apertures form a full aperture and a size of each of the first sub-aperture and the second sub-aperture is in a range of 50%-80% of a size of the full aperture.

6. The apparatus of claim 1, wherein the one or more processing devices are formed in an FPGA or an ASIC.

7. The apparatus of claim 1, wherein the one or more processing devices are configured to determine output data for imaging the target tissue at an additional point by:
processing a plurality of portions of additional ultrasound signals associated with the additional point in the target tissue, wherein each of the plurality of portions of additional ultrasound signals is associated with a respective one of the plurality of sub-apertures of the transducer array, and wherein the processing comprises:
determining a respective coherent sum over each of the plurality of portions of the additional signals associated with the additional point in the target tissue; and
performing the processing operation over the respective coherent sum to obtain respective resulting data for each of the plurality of portions of the additional ultrasound signals; and
determining output data for imaging the target tissue at the additional point by summing the resulting data for the plurality of portions of the additional signals.

8. The apparatus of claim 1, wherein the handheld ultrasound probe is configured to perform cardiac ultrasound imaging and wherein the ultrasonic transducer array is configured to selectively transmit ultrasound signals at frequencies between 1 MHz and 5 MHz.

9. A method of processing ultrasound signals received by an ultrasonic transducer array for imaging a target tissue, the method comprising, for a point in the target tissue:
processing a plurality of portions of ultrasound signals associated with the point in the target tissue, wherein each of the plurality of portions is grouped into to a respective one of a plurality of sub-apertures of the transducer array, wherein the received ultrasound signals are each delayed by a respective delay time, and wherein the processing comprises:
determining a respective coherent sum over each of the plurality of portions of the ultrasound signals for each sub-aperture;
performing a processing operation over the respective coherent sum to obtain respective resulting data for each sub-aperture; and
normalizing the respective resulting data for a sub-aperture of the plurality of sub-apertures by an incoherent sum of the received ultrasound signals associated with the sub-aperture; and
determining output data for imaging the target tissue at the point by summing the normalized resulting data for the plurality of sub-apertures.

10. The method of claim 9, wherein the processing operation comprises at least in part a square operation or a magnitude square operation.

11. The method of claim 9, wherein at least a first sub-aperture of the plurality of sub-apertures is overlapped with a second sub-aperture of the plurality of sub-apertures.

12. The method of claim 11, wherein the plurality of sub-apertures form a full aperture and a size of each of the first sub-aperture and the second sub-aperture is in a range of 50%-80% of a size of the full aperture.

13. The method of claim 9, further comprising, for an additional point in the target tissue:
processing a plurality of portions of additional ultrasound signals associated with the additional point in the target tissue, wherein each of the plurality of portions corresponds to a respective one of the plurality of sub-apertures of the transducer array, wherein the additional ultrasound signals are each delayed by a respective delay time, and wherein the processing comprises:
determining a respective coherent sum over each of the plurality of portions of the additional ultrasound signals; and
performing a processing operation over the respective coherent sum to obtain respective resulting data for each sub-aperture; and
determining output data for imaging the target tissue at the additional point by summing the resulting data for the plurality of sub-apertures.

* * * * *